United States Patent
Ruddle et al.

(10) Patent No.: US 8,970,618 B2
(45) Date of Patent: Mar. 3, 2015

(54) VIRTUAL MICROSCOPY

(75) Inventors: Roy Ruddle, Leeds (GB); Darren Treanor, Leeds (GB)

(73) Assignees: University of Leeds, Leeds (GB); The Leeds Teaching Hospitals NHS Trust, Leeds (GB)

( * ) Notice: Subject to any disclaimer, the term of this patent is extended or adjusted under 35 U.S.C. 154(b) by 6 days.

(21) Appl. No.: 13/492,777

(22) Filed: Jun. 8, 2012

(65) Prior Publication Data

US 2012/0320094 A1 Dec. 20, 2012

Related U.S. Application Data

(60) Provisional application No. 61/497,862, filed on Jun. 16, 2011.

(51) Int. Cl.
*G09G 5/00* (2006.01)
*G06F 19/00* (2011.01)
*G02B 21/36* (2006.01)
*G06T 7/00* (2006.01)

(52) U.S. Cl.
CPC .......... *G06F 19/321* (2013.01); *G02B 21/367* (2013.01); *G06T 7/0024* (2013.01); *G06T 2207/10056* (2013.01); *G06T 2207/20092* (2013.01); *G06T 2207/30024* (2013.01)
USPC .......... 345/619; 345/660; 382/128; 382/132; 382/133

(58) Field of Classification Search
USPC .......... 345/619, 660; 715/771, 731, 732, 838; 382/128, 132, 133; 348/79
See application file for complete search history.

(56) References Cited

U.S. PATENT DOCUMENTS

| | | | | |
|---|---|---|---|---|
| 6,396,941 B1 * | 5/2002 | Bacus et al. | ................... | 382/128 |
| 7,292,251 B1 * | 11/2007 | Gu et al. | ................... | 382/128 |
| 2003/0210262 A1 * | 11/2003 | Gahm et al. | ................... | 345/732 |
| 2004/0252875 A1 * | 12/2004 | Crandall et al. | ................... | 382/133 |
| 2005/0254696 A1 * | 11/2005 | Bacus et al. | ................... | 382/128 |
| 2006/0050948 A1 * | 3/2006 | Sumida et al. | ................... | 382/133 |
| 2006/0276974 A1 * | 12/2006 | Zeineh et al. | ................... | 382/128 |

(Continued)

FOREIGN PATENT DOCUMENTS

| | | |
|---|---|---|
| JP | 2006-145857 | 6/2006 |
| WO | 98/39728 | 9/1998 |

(Continued)

OTHER PUBLICATIONS

Search Report received by European counsel on Oct. 9, 2012 for Application No. EP 12 17 2390.

(Continued)

*Primary Examiner* — Chante Harrison
(74) *Attorney, Agent, or Firm* — Beyer Law Group LLP

(57) ABSTRACT

Computer implemented methods and data processing apparatus are described for displaying virtual slide images. Images of a plurality of slides are automatically displayed in a first region of a display device at a first magnification. The slides comprise all the slides including material from a same specimen. An image of at least one of the slides is displayed in a second region at a second magnification greater than the first magnification. At least the image displayed in the second region is changed responsive to receiving user input. Methods for automatically determining a slide layout pattern and methods for virtually melding glass slide images into a single image are also described.

22 Claims, 15 Drawing Sheets

(56) References Cited

U.S. PATENT DOCUMENTS

| | | |
|---|---|---|
| 2009/0006969 A1 | 1/2009 | Gahm et al. |
| 2009/0212242 A1 | 8/2009 | Yamada |
| 2010/0031152 A1* | 2/2010 | Villaron et al. ............... 715/731 |
| 2010/0073472 A1* | 3/2010 | Zeineh et al. ................... 348/79 |
| 2011/0037847 A1 | 2/2011 | Soenksen |
| 2011/0060766 A1* | 3/2011 | Ehlke et al. ................... 715/771 |
| 2011/0131535 A1* | 6/2011 | Tagami et al. ................ 715/838 |
| 2012/0044342 A1* | 2/2012 | Hing et al. ..................... 348/79 |
| 2014/0068442 A1* | 3/2014 | Eichhorn et al. .............. 715/732 |

FOREIGN PATENT DOCUMENTS

| | | |
|---|---|---|
| WO | 01/26541 | 4/2001 |
| WO | 01/54052 | 7/2001 |

OTHER PUBLICATIONS

Search Report received by European counsel on Oct. 23, 2012 for Application No. GB1210743.9.

* cited by examiner

VIRTUAL MICROSCOPY

CROSS REFERENCE TO RELATED APPLICATIONS

This application claims benefit of U.S. Provisional Application No. 61/497,862, filed Jun. 16, 2011, which is hereby incorporated herein by reference.

BACKGROUND OF THE INVENTION

A number of virtual microscopy software packages and hardware systems, and parts thereof, are already known. For example Aperio Technologies, Inc. provide digital slide scanners, a viewing software application and information management software. Similarly digital pathology systems are provided by Omnyx LLC, Leica Microsystems and Koninklijke Philips Electronics N.V.

While virtual microscopy is already established and virtual slide image viewing software is already available, such viewing software is not necessarily tailored to improve the efficiency with which a user may view slide images and carry out their work, for example, a pathologist making a diagnosis.

Also, virtual slide images can be captured by scanners at very high resolution and so the resulting image data files can be very large, for example hundreds of megabytes or a few gigabytes. There can therefore be issues in handling such large data files in efficient ways both to improve efficiency of use of the image viewing software by a user and also how the image viewing software itself handles such large amounts of data.

It would therefore be beneficial to provide image viewing software for virtual slides which allows a user to more efficiently use the viewing software to view slides and/or to increase the efficiency or reliability of the viewing software.

FIELD OF THE INVENTION

The present invention relates to virtual microscopy and in particular to viewers for virtual slides.

BRIEF SUMMARY OF THE INVENTION

A first aspect of the invention provides a method for displaying virtual slide images on a display device of a virtual slide viewing device. The method can comprise automatically displaying images of a plurality of slides in a first region of the display device at a first magnification. The plurality of slides are associated. An image of at least a part of at least one of the plurality of slides can be displayed in a second region of the display device at a second magnification. The second magnification can be greater than the first magnification. The method can also include receiving user input to the virtual slide viewing device. At least the image displayed in the second region can be changed or altered responsive to said user input and as indicated by the user input.

Hence, the first region provides an overview of all slides including material from the specimen currently being reviewed and the second region displays images at a higher level of magnification. The first region can therefore be used to more easily navigate amongst the higher magnification images being displayed in the second region.

The plurality of slides can include material from one specimen or a plurality of specimens.

The plurality of slides may comprise some or all of the slides of a same specimen or different specimens.

The slides for each specimen may have come from the same or different patients or subjects.

The plurality of slides can comprise some or all of the slides from the same specimen or the same subject. The subject may be a patient.

The method can further comprise displaying an image of at least a part of at least one of the plurality of slides in a third region of the display device. The image can be displayed at a third magnification. The third magnification can be greater than said first magnification and less then said second magnification. The third region can display images at an intermediate level of magnification between that used to display images in the first region and second region.

Said user input can be a command to change the manner of display of the image or the part of the image being displayed. The command can be selected from: a pan command; a zoom command; and a select command.

The user input can be generated by user interaction with, e.g. a cursor being positioned in, the first region and/or the second region and/or the third region. Hence, any of the image display regions can be used to accept user input to alter the images being displayed in the second and/or third regions.

The method can further comprise displaying a visual indication in the first region of those parts of the slides displayed in the first region which are also currently being displayed in the second region.

The method can further comprise providing a memory management mechanism. The memory management mechanism can include identifying some data as not being overwritable in memory and some data as being overwritable. A data structure can be stored in memory which includes data items indicating whether image data is overwritable or not. A plurality of different portions of image data can be loaded into local memory of the virtual slide viewing device. At least one of the portions of image data can be flagged as persistent or not-overwritable so that the portion of image data is not overwritten while the current plurality of slides are being displayed. At least one of the portions of image data can be flagged as non-persistent or overwritable so that the portion of image data can be overwritten while the current plurality of slides are being displayed. Image data to be overwritten can be selected based on image data which is flagged as non-persistent and which has been displayed least recently.

Image data for each virtual slide can be stored at a plurality of different levels of magnification. The image data for each different level of magnification can be divided into a plurality of different portions, or tiles, of image data.

Displaying an image of at least a part of at least one of the plurality of slides in a region of the display device can comprise reading only those portions, or tiles, of image data corresponding to parts of the slide which would be visible in the region. The region can be the first region and/or second region and/or third region of the display device. This reduces rendering time as only those parts of the data relating to the slide image which needs to be displayed are read for image rendering, rather than all of the image data for that slide.

The method can further comprise storing a pointer to a location in local memory at which the portion of image data is stored, for each of a plurality of portions of image data. This provides direct access to the area of memory in which the image data is stored thereby reducing data retrieval time.

The method can further comprise persistently storing in local memory all the image data required to display all of the plurality of slides in a region at a particular level of magnification. The region can be the first region and/or second region and/or a third region of the display device. The storing can be carried out while the viewer is being used to display the plurality of slides at a different magnification level. Hence, image data is always locally available to display any part of all the slides at the particular level of magnification. The particular level of magnification can be a higher level of magnification than that used for the first region and/or different to the level of magnification initially used for displaying images in the second region.

The method can further comprise loading into local memory of the image viewing device image data for the plurality of slides at a level of magnification different to the level of magnification currently being used in the second region while said image of at least a part of at least a one of the plurality of slides is being displayed in the second region. Hence, image data can be pre-fetched in the background so that it is immediately available for rendering images of the slides at a different level of magnification in the second region. The different level of magnification is preferably greater than the level of magnification initially used to display images in the second region.

The method can further comprise downloading image data for the plurality of slides from a remote storage device over a network. The method can further comprise compressing the image data before transmitting over the network. The method can further comprise decompressing the downloaded image data at the virtual slide viewing device, if the image data was transmitted in compressed form over the network.

A second aspect of the invention provides a method for displaying virtual slide images on a display device of a virtual slide viewing device. The method can comprise identifying a plurality of slides to be displayed in a single region of a display device. The plurality of slides can comprise all the slides having material from a same specimen. A layout pattern can be automatically determined based on attributes associated with the slides. Images of the plurality of slides can be automatically displayed in the single region of the display device in the layout pattern. The layout pattern can encode information about the plurality of slides in a visually discernable form.

By encoding information about the slides into the layout pattern, it is easier for a user to determine and select which slides to view, out of all of the slides available to view, more efficiently in order to carry out their assessment.

The layout pattern can encode clinical information about the plurality of slides. The clinical information can comprise information used by a pathologist in assessing the slides.

The method can further comprise displaying information about the tissue of each slide for each slide and adjacent to each slide. The information can be displayed as part of a visual representation of the slide, e.g. as part of a header or a title of a slide.

The method can further comprise displaying information about a stain used to stain tissue of a slide for each slide. The information about a stain can be colour coded. A different colour can be used for each different stain or different type of stain. Colour coding can be accomplished by displaying at least a part, or the whole, of each slide including a stained sample in a particular colour.

Automatically determining the layout pattern can comprise applying a plurality of layout rules using the attributes of the plurality of slides. It can be determined whether the resulting layout pattern meets one or more layout criteria. If so then the resulting layout can be used. If not then one of the layout rules can be relaxed or removed. The layout rules can be hierarchical. The layout rules can be assigned different levels of precedence. The rule with the lowest precedence can be relaxed or removed first. The rules can be relaxed or removed in an order corresponding to their precedence, i.e. least precedence first.

The layout rules can include one or more rules selected from: when to start a new line of slides; when to indent a new line of slides; when to group a plurality of slides; what attributes to use to define a group of slides; what level of magnification to use to display the slides; and the aspect ratio of the layout pattern.

The layout rules can be user configurable. A default set of layout rules can also be provided.

A third aspect of the invention provides a method for displaying virtual slide images on a display device of a virtual slide viewing device. The method can include displaying a first slide image and a second slide image in a first region of the display device. User input can be received to manipulate at least a part of the first slide image or at least a part of the second slide image to form the images of the pieces of material into a single image.

Hence, the method can be used to generate and display a single image of material which is initially displayed as separate slides.

The first slide image and the second slide image can each include an image of a part of the same part or slice of a material. User input can be received to manipulate at least a part of the first slide image or at least a part of the second slide image to form the images of the parts of the same slice or part of material into a single image of the same slice or part of material.

The method can further comprise displaying the single image in a second region of the display device. The single image can be displayed in the second region of the display device at a higher level of magnification than the images displayed in the first region.

The method can further comprise receiving user input selecting at least a portion of the image of the part of the piece of material from the first slide image. User input can also be received selecting at least a portion of the image of the piece of material from the second slide image. The selected portion of the image of the piece of material of the first slide image and the selected portion of the image of the piece of material of the second slide image can be displayed in a further display region of the display device.

The user input can be generated by user interaction with the images displayed in the further display region.

The user input can be selected from: rotation; translation; and changing size.

A further aspect of the invention provides a virtual slide image viewing device, configured to carry out any of the method aspects of the invention. The device can include a display device and a data processing device in communication with the display device. The data processing device can be configured to carry out any of the method aspects of the invention and/or preferred features or combinations of features thereof.

A yet further aspect of the invention provides a computer readable medium storing in a non-transitory way computer program code or codes which when loaded into a data processing device configures the data processing device to carry out any of the method aspects of the invention and/or preferred features or combinations of features thereof.

A yet further aspect of the invention provides a user interface for a virtual slide viewer having features corresponding to the features of any of the preceding method aspects of the invention and/or preferred features or combinations of features thereof.

A yet further aspect of the invention provides a virtual microscopy method or method for displaying virtual slide images of a specimen or specimens. The method may include preparing a plurality of slides including material from the specimen or specimens. Virtual slide image data can then be generated from the physical slides, for example by scanning the physical slides. The virtual slide image data can then be stored. The virtual slide image data can then be displayed and/or viewed using any of the method, apparatus, computer readable media or user interface aspects of the invention. The displayed images may be assessed by a user.

DETAILED DESCRIPTION OF THE INVENTION

Figure 1:
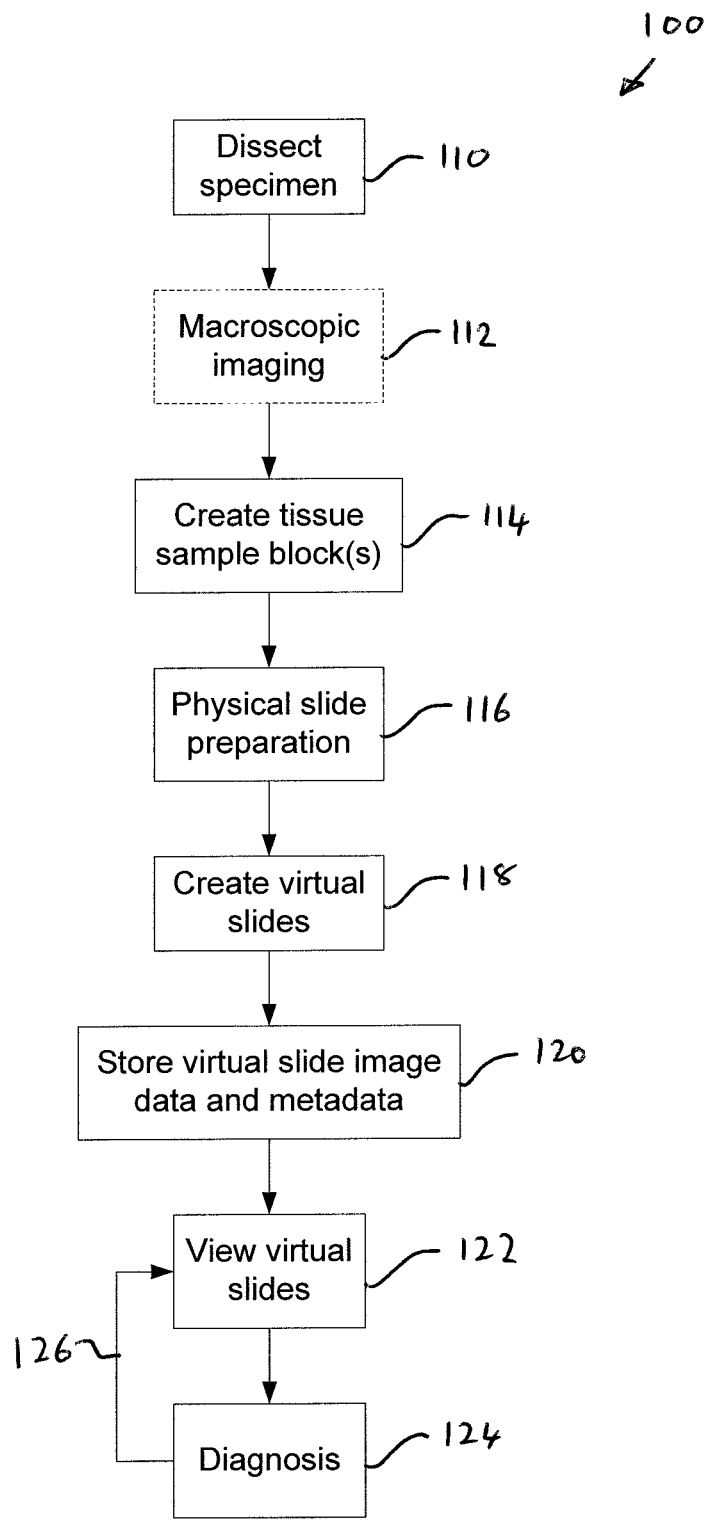
FIG. 1 shows a flow chart illustrating a typical pathology method in which the viewer of the invention can be used.

With reference to FIG. 1 there is shown a flow chart illustrating a pathology method 100, at a high level, in which the viewer of the invention may be used. It will be appreciated that the invention is not limited to use in such pathology applications. Rather, the viewer can be used in all virtual microscopy applications and indeed in all applications in which it is useful to be able to view a large number of related images in an efficient manner.

Although the invention will be described within the context of digital pathology, the invention is not limited to that field of application. Also, the embodiment will be described when applied to a single specimen. However, it will be appreciated that in some embodiments it may be useful to view slides having tissue from different specimens. Those different specimens may be from the same patient or from different patients. For example, a pathologist may want to look at different specimens from the same patient or look at the same type of specimen but from different patients.

The method 100 begins with the laboratory receiving a specimen for a patient who has undergone a procedure. The procedure associated with a mastectomy (i.e. the pathology specimen obtained by surgical removal of the breast) will be used purely as an example, and the invention is not limited thereto. A single specimen will be received by the laboratory for a particular procedure carried out on the patient. However, it will be appreciated that a particular patient may have multiple specimens processed over time with a different specimen from different procedures. At step 110, the specimen is dissected into one or more parts. For example, a first part may include tissue from the skin of a breast and a second part may contain tissue from the interior of the breast. Optionally, as illustrated by dashed line, at step 112, a macroscopic image of the specimen or parts thereof may be captured.

At step 114, one or more tissue sample blocks are created by the histopathologist. Each part may be cut into multiple tissue pieces of the part. The tissue pieces are then embedded in a paraffin block to produce a tissue block of uniform size. A tissue block can have more than one tissue piece within it and tissues pieces from more than one area of tissue can be provided in the same block. After the tissue block or blocks have been created at step 114, the physical slides are prepared at step 116 for scanning. The tissue blocks are cut to form thin sections (approximately 2 to 7 micrometers thick) which are then mounted on a glass microscope slide. Once the sections have been mounted on the glass slides, they can then be stained using stains, such as standard stains, special stains or immunohistochemical stains. For example, standard stains include the 'H&E stain' (haematoxylin and eosin). Special stains are non-routine histochemical stains and are used to identify specific tissue components or organisms that are less easily identifiable with an H&E stain. It is also possible to use immunohistochemical stains which target specific antigens within tissue in order to visualise the presence of absence of highly specific proteins within tissue.

Once the physical slides have been prepared, then at step 118, virtual slides are created by scanning the physical slides using a virtual slide scanner. A suitable device includes the ScanScope XT as provided by Aperio Technologies, Inc. of California, USA. (ScanScope XT is a trademark of Aperio Technologies, Inc. which may be registered in some countries). The scanner generates a high resolution image of each slide for subsequent display and viewing. The digital image of the slide is the virtual slide which is subsequently viewed and handled by the virtual microscopy system and viewer.

At step 120, the virtual slide image data or all of the slides relating to the specimen and the clinical details for the specimen (referred to generally as the "case") are stored in various databases, together with metadata about the virtual slide.

Following step 120, the virtual slide is available for viewing. Hence, at step 122 a viewer software application can be used to view the virtual slides and at step 124, a user of the viewer can carry out a diagnosis by viewing and manipulating the images of the virtual slides. The diagnosis and viewing is an iterative process, as illustrated by process flow line 126 intended to illustrate the repeated viewing and manipulation of virtual slides of the currently configured case.

Figure 2:
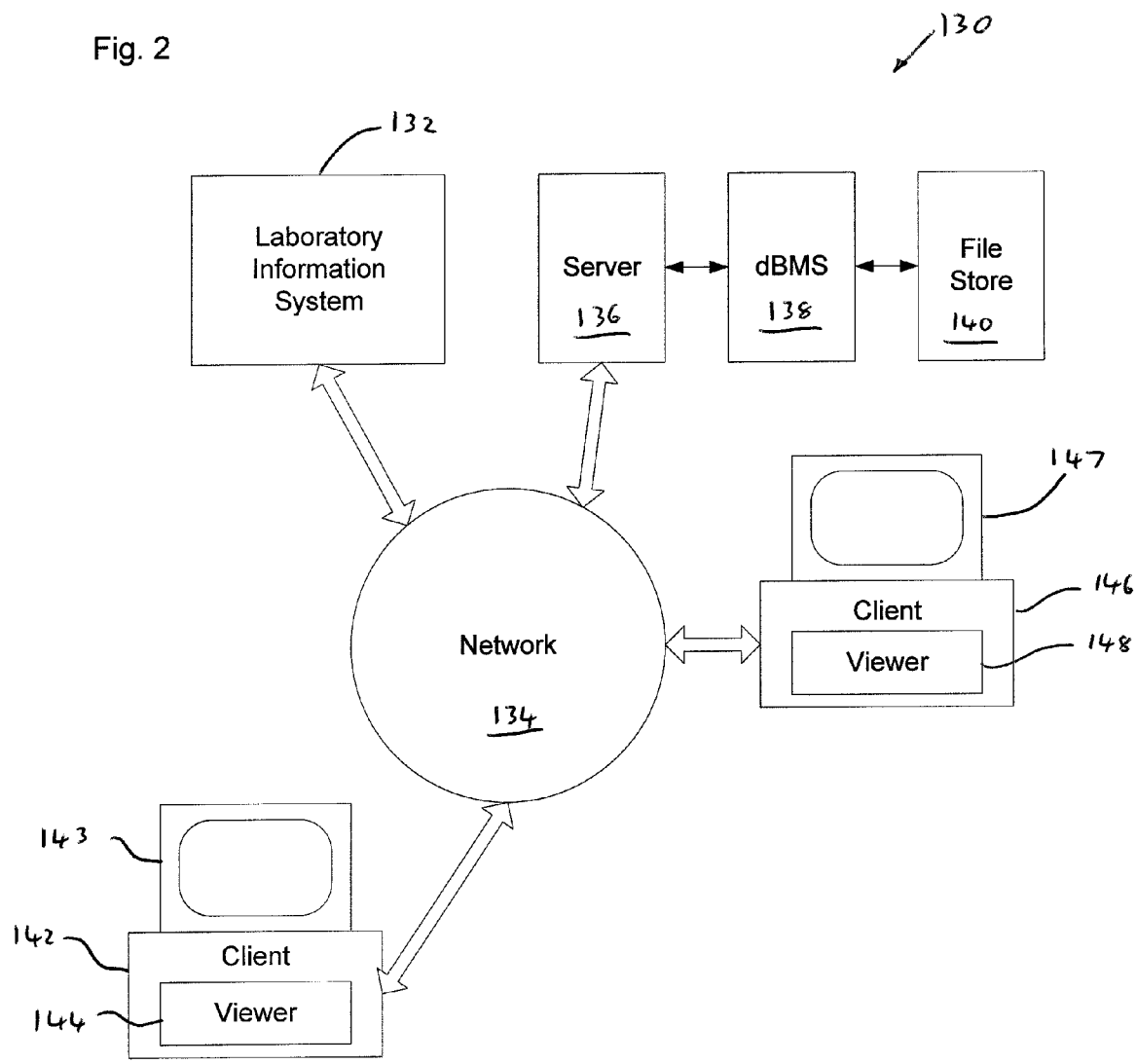
FIG. 2 shows a schematic block diagram of a computer system according to the invention and including a viewer device according to the invention and viewer software according to the invention.

FIG. 2 shows a schematic block diagram illustrating a computer system 130 which can be used as part of the virtual microscopy method. Computer system 130 includes a laboratory information system part 132 which itself includes various databases and data processing components. Laboratory information systems (LIS) are generally well known and are not described in further detail herein apart from as required in order to understand the invention. LIS 132 is in communication with a communication network 134. The exact nature of the network is not important and depending on the embodiment may be a local area network, wide area network and include wired and/or wireless network components. In some embodiments, the network is the internet.

Computer system 130 includes a viewer server 136 configured to operate to service requests from a client viewer application. Viewer server 136 is in communication with a database management server 138 which in turn is in communication with a file server 140 which provides a file store for storing the scanned image data of the virtual slides. Database management server 138 interacts with viewed server 136 and file server 140 to service requests for image and metadata from server 136 by accessing the file store 140.

A viewer software application, according to the invention, can operate locally on a client computing device 142, with associated display device 143, and is illustrated by data processing entity 144. A second client computing device 146, also having a display device 147, can also access the virtual microscope system and can have its own separate instance of viewer represented by software entity 148. Client computing devices 142 and 146 can independently display virtual slides on their respective display devices 143, 147.

Figure 3:
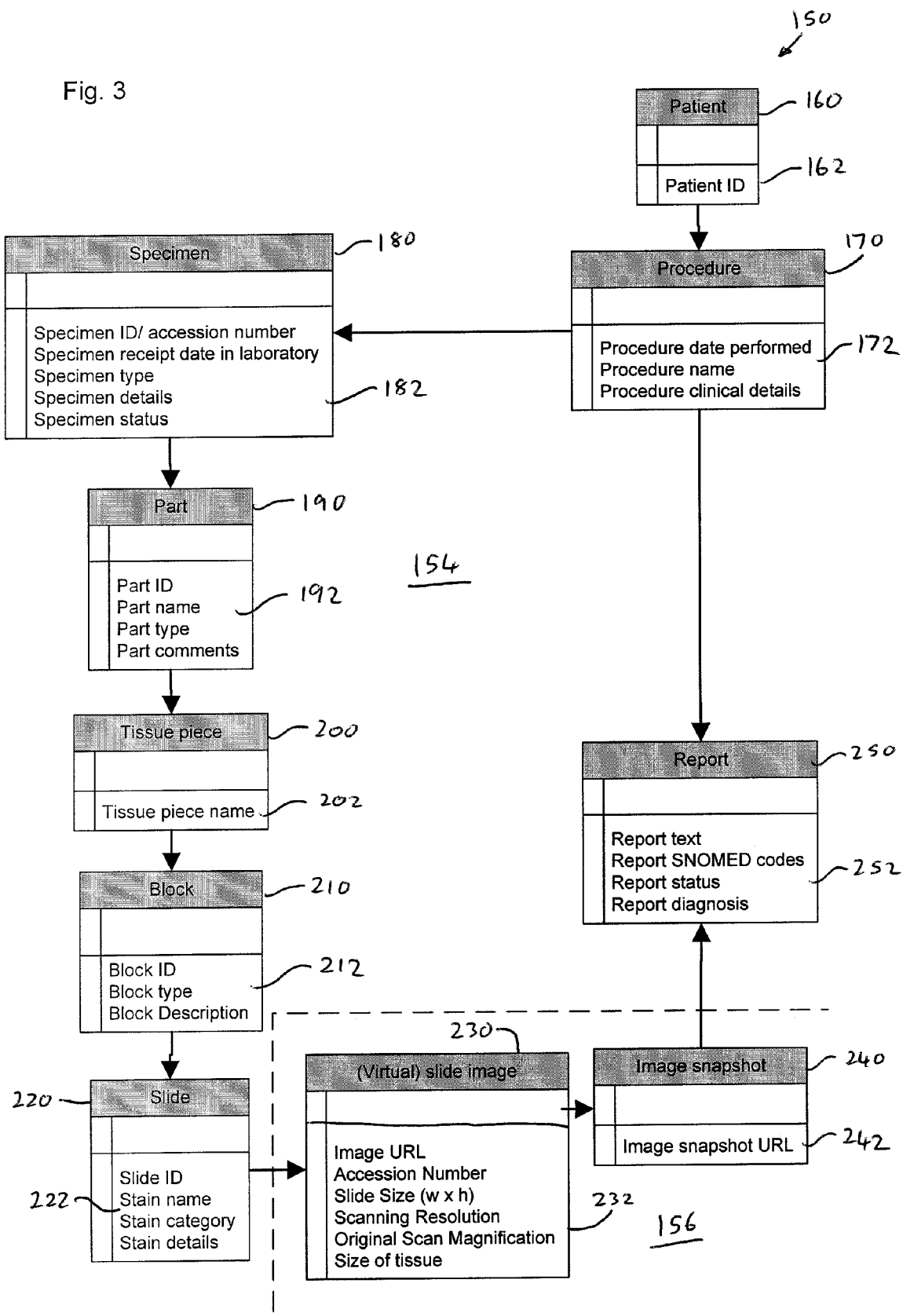
FIG. 3 shows an entity relationship diagram for data present in databases of the system shown in FIG. 2.

FIG. 3 shows an entity relationship diagram 150 illustrating the various data items provided by the LIS and file store 140. It will be appreciated that depending on the embodiment, various data items may be omitted or added. The entity relationship diagram illustrates a plurality of tables each storing various data items usable by the computing system 130. Some of the tables are provided as part of the LIS 132. Others of the data items are provided by the file store 140. Dashed line 152 illustrates the segregation between tables 154 provided by LIS 132 and tables 156 provided by file store 140. However, as server 136 can communicate with LIS 132 via network 134, server 136 has access to the data items of LIS 132 as needed.

A patient table 160 stores various data items relating to individual patients and includes a patient ID data item 162 providing a unique identifier for each patient.

A procedures table 170 stores various data items relating to each procedure carried out for a particular patient. The procedure data items 172 include a date on which the procedure was carried out, the name of the procedure, and any clinical details associated with that particular procedure.

A specimen table 180 stores various data items relating to the particular specimen for a particular procedure. The specimen data items 182 include data items indicating the specimen ID/accession number which is the unique identifier for a particular specimen. Specimen data items 182 also include a date of receipt of the specimen in the laboratory, an indication of the type of the specimen, details of the specimen and the current status of the specimen (being its current position or status in the laboratory workflow).

A part table 190 stores data items relating to each individual part of a particular specimen. The part data items 192 include data items relating to a unique identifier for each part, the part name, the part type and a free text field for comments on the part.

A tissue piece table 200 stores data items relating to each tissue piece cut from a part. The tissue piece data items include a data item relating to the name of each tissue piece.

A block table 210 stores data items relating to each block in which a tissue piece or pieces have been embedded. The block data items 202 include a block identifier (or block ID) for each block and a block type data item indicating the type of the block. Block table also includes a block description data item which provides a description of the material in the block and which can be used subsequently to provide enhanced information about the slides in the slide layout as described below with reference to FIG. 12. Alternatively, the Tissue piece name field in the Tissue piece table could be used to hold this information.

A slide table 220 stores data items relating to the section of tissue on each physical slide. The slide data items 222 include a slide identifier (or slide ID), a name for a stain applied to the tissue, the category of stain applied to the tissue and any details about the stain used.

A slide image table or virtual slide table 230 stores various data items relating to the scanned image of the physical slide. The virtual slide data items 232 include a data item directly or indirectly identifying the location of the stored image data (image URL (Uniform Resource Location)), for each individual slide. The virtual slide data also includes the accession number for the specimen, as also present in table 180, and various data relating to the scanning of the slide, such as the physical size of the glass side, the scanning resolution, the magnification of the original scan and the size of the tissue sample on the slide. Some of this data may be captured automatically by the scanner and some of the data may be manually input or retrieved from LIS.

An image snapshot table 240 may also be provided to store image about a snapshot image captured of the virtual slide. The image snapshot data items 242 include at least a data item providing a direct or indirect indication of the location at which the image file is stored.

A report table 250 is also provided and stores data used to prepare a report on the case. The report data 252 includes data relating to the text of the report, SNOMED codes, the status of the report and a summary of the diagnosis of the report. As illustrated in FIG. 3, the report table may include items from the file store tables 156 as well as from the LIS tables 154.

Figure 4:
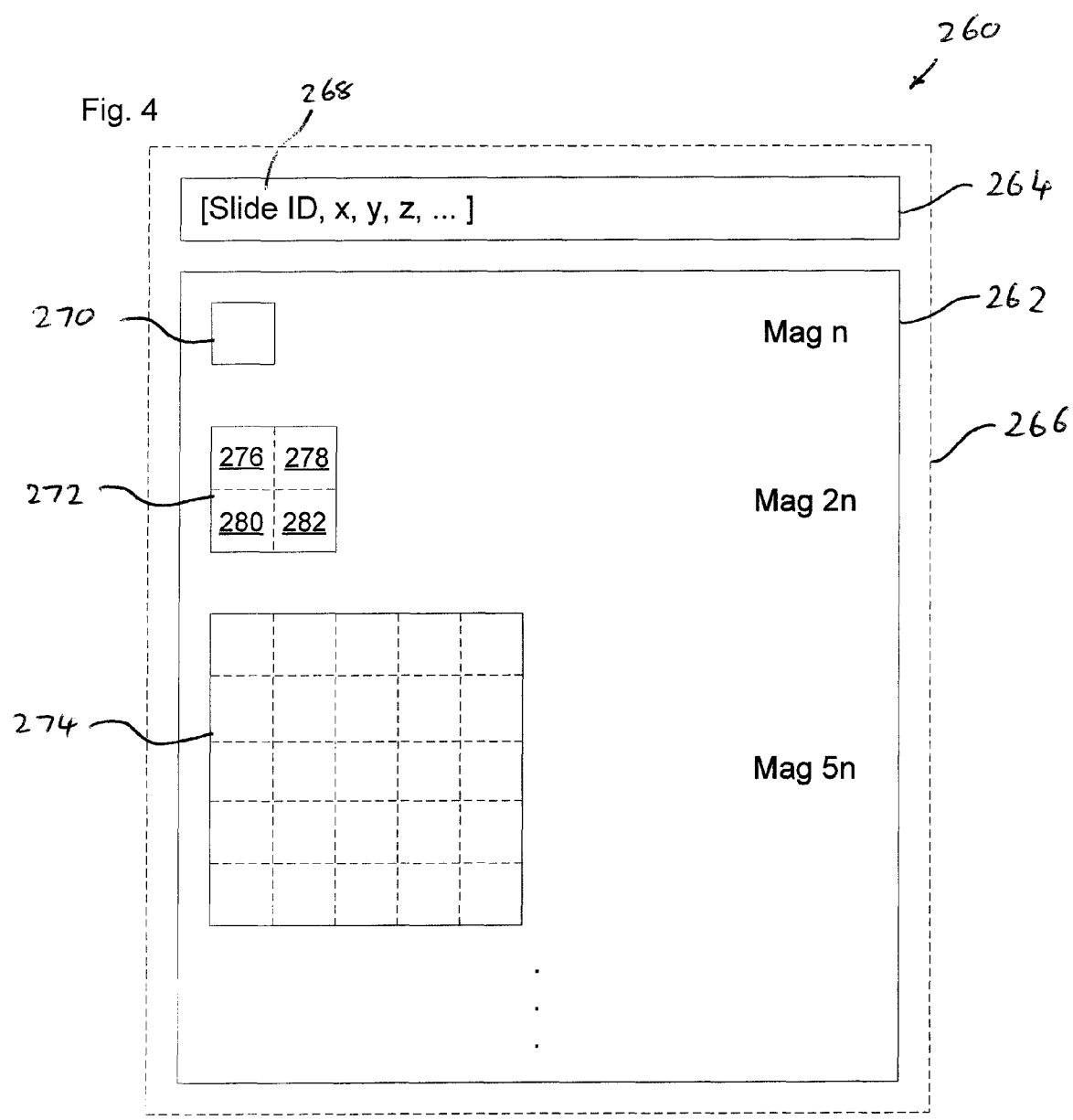
FIG. 4 shows a schematic visual representation of a slide scan image data file as used in the invention.

FIG. 4 shows a visual representation of the data associated with a virtual slide 260. Conceptually, the virtual slide includes scanned slide image data 262 and also slide data 264 associated with the image data 262, which may include metadata about the virtual slide. As illustrated by dashed line 266, the slide image data 262 and slide data 264 associated with the image data are somehow associated and do not need to be co-located or stored in the same file. Some of the slide data 264, e.g. slide ID data item 268, may be stored by the LIS 132 and other data items, such as the data items stored in table 230, may be stored on file store 140.

The virtual slide image data 262 includes multiple images of the slide at different levels of magnification. Scanned slide image data 270 is at a first, low level magnification (n) (e.g. suitable for a thumb-nail image), scanned slide image data 272 is at a higher level of magnification (2n) and scanned slide image data 274 is at a yet higher level of magnification (5n). Scanned slide image data at yet higher levels of magnification may also be included in the virtual slide image data 262.

As also illustrated in FIG. 4, the scanned slide image data for each level of magnification is composed of a plurality of individual groups or portions of image data, referred to generally as "tiles". The lowest magnification image data 270 (corresponding to magnification n) comprises only a single tile, whereas image data 272 comprises four tiles of image data 276, 278, 280, 282.

The use of tiles to break down the larger blocks of image data greatly improves the efficiency of data transfer over the network from file store 140 to viewer 144 as will be described in greater detail below.

Storage of the scanned slide image data at differing levels of magnification is generally referred to herein as a "pyramidal" image file structure and also greatly enhances the responsiveness of the viewer to requested changes in display of slide images as will also be described herein. The specific format of the slide image data can vary depending on the embodiment and can include JPEG, TIF or DICOM standards or other proprietary formats can be used.

Operation of the virtual slide viewer application 144 will now be described in greater detail. Typically, a user of client computing device 142 will be accessing the LIS 132 over network 134. If the user decides to view virtual slides using the display device 143, 147 of their client computing device 142, then they enter a command into the client device 142. If the user is currently accessing information about a particular case, then the LIS 132 communicates with client device 142 via network 134 to spawn an instance of the viewer application 144 on the client computing device 142. Also, the LIS 132 sends the accession number for the current case, a list of all the slides for the specimen (or specimens) for the current case and metadata relating to these slides to the client device 142 over network 134. The local viewer application 144 has a local copy of virtual slide table 230 for each slide and therefore has immediate access to relevant data relating to each slide and also a direct pointer or link to the location of the relevant image data on file store 140 (provided by the image URL data item) via viewer server 136.

The image data stored in the file store is very large. For example, a high resolution slide image can have a resolution of 100,000 by 80,000 pixels. Such high resolution images are beyond the limits of most image viewers to open in their entirety. Image data from can be transferred in a compressed or non-compressed format from the file store to the client 142, via server 136. If the image data is transmitted in a compressed format, then the viewer 144 decompresses the received image data for local display. As explained in greater detail below, the system transfers only those parts of the image data required for immediate display so as to reduce network traffic, viewer memory and processor utilisation. Also, a memory management mechanism is put in place to prevent memory overflow when handling such large amounts of image data.

Figure 5:
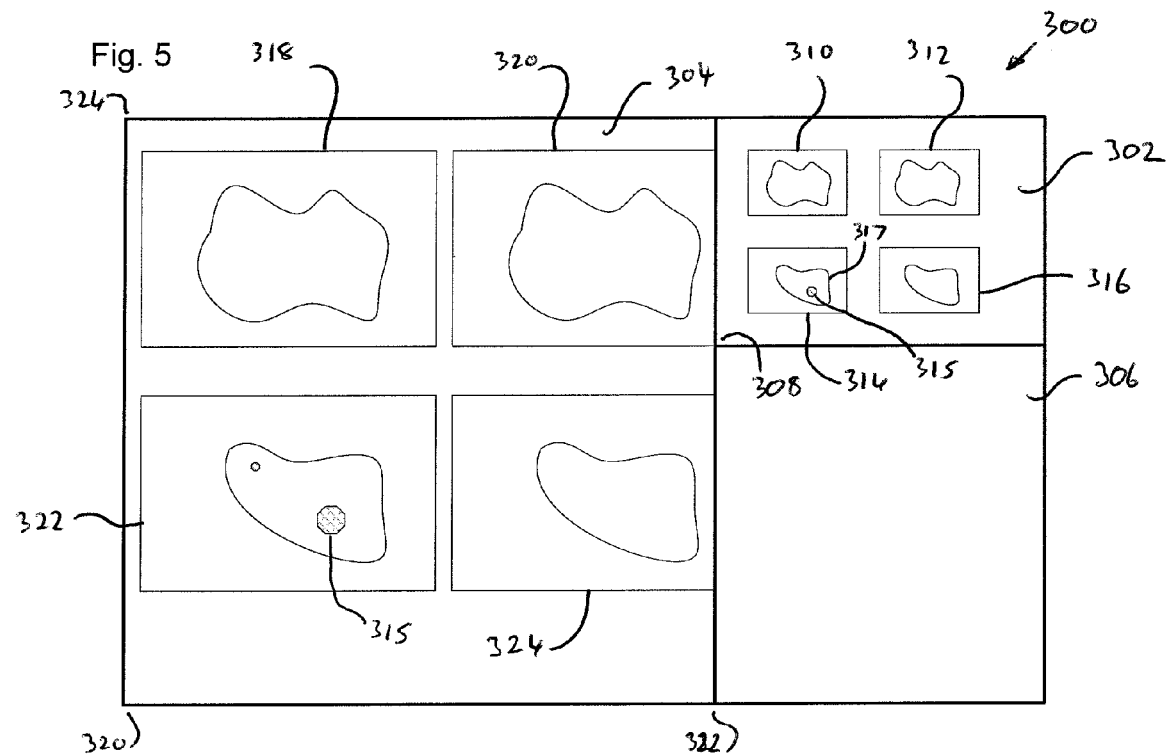
FIG. 5 shows a schematic visual representation of a user interface of the viewer as displayed on a display device of the system of FIG. 2.

When the image viewer is opened, an initial view of the case is presented to the user, as illustrated in FIG. 5. FIG. 5 shows a schematic illustration of a user interface 300 of the image viewer application as displayed on a display device of client computer 142. The user interface 300 may include various control elements which are omitted from the Figures for the sake of clarity. The user interface of viewer 144 includes a first display region 302. On opening the viewer, the first display region 302 is automatically populated with low magnification images of all of the slides in the case, as described in greater detail below. However, in other embodiments, the first display region may automatically be populated with just a sub-group of all of the slides for a case or with a plurality of slides from different cases. The user interface 300 includes a second display region 304. The second display region 304 displays images of at least one or more of the slides of the case, but at a higher magnification than those shown in the first display region.

The user interface 300 can also include a third display region 306. The third display region can be used for a variety of purposes as will be described in greater detail below. The third display region 306 can be used to display images of tiles or parts of tiles at an intermediate magnification between that of the first and second display regions. The third display region 306 can also be used to manipulate virtual slides as also described in greater detail below.

Figure 7:
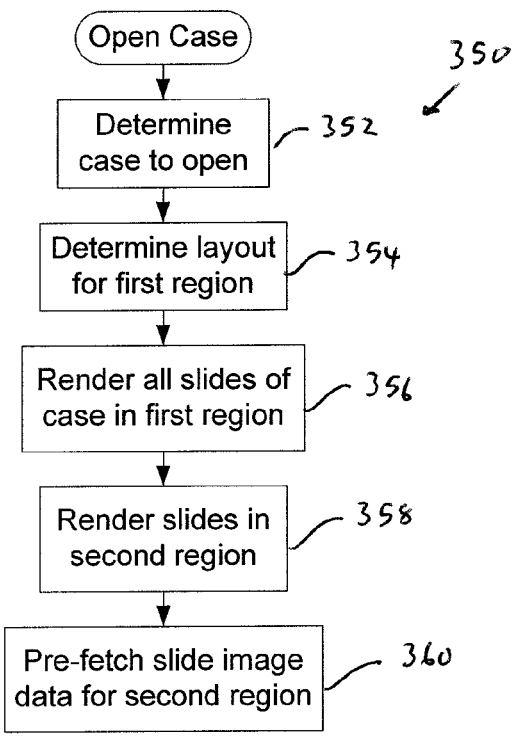
FIG. 7 shows a process flow chart illustrating a method of opening a case in the viewer according to the invention.

FIG. 7 shows a process flow chart illustrating a method 350 of opening a case and generating the initial user interface 300 as illustrated in FIG. 5. At step 352, it is determined which case is to be opened. As described above, this can be achieved by the LIS retrieving the accession number or specimen ID for the case currently under consideration and passing the accession number to the viewer application. LIS can also pass a sequential list of all the virtual slides comprising the case by passing a list of slide ID data items for that accession number. Hence, the main programme thread of viewer application 144 now has the accession number and slide ID data items for every slide within the current case. The slide ID data items can be used to access the virtual slide table 230 to determine the metadata relating to the slide images and slide image location.

At step 354, the main programme thread of viewer application 144 determines the layout of the plurality of slides to be displayed in the first region 302. This low magnification first region 302 is sometimes referred to herein as the "world view". That is, the first region is used to provide an overview of the entire "world" of slides comprising the current case. This allows the case as a whole to be assessed which provides an overview that is not possible with software which displays individual slides nor which requires manual interaction in order to display multiple ones of the slides. The world view is a continuous area of display 302 into which low resolution images of all of the slides are automatically rendered by the viewer application. This is particularly beneficial for the type of assessments that are typically carried out at the low magnification or require a diagnosis which builds up information over a series of slides.

An example of the process for automatically determining the layout of the first region is described in greater detail below with reference to FIGS. 11 and 12.

Once the layout of the slides in the first region has been determined, then at step 356, the viewer application automatically renders images of all of the slides of the case in the first region 302. For example, as illustrated in FIG. 5, the case includes four separate slides and therefore, initially, four low resolution images are rendered and displayed in first region 302.

The first display region 302 (sometimes referred to herein as the 'world view' region) has its own coordinate system defined with an origin at point 308 in region 302 and a horizontal X position and vertical Y position extending to the side and upper boundaries. Each individual slide image 310, 312, 314, 316 has a position within that world coordinate system. Each slide has its own internal coordinate system, again with an origin at its bottom left hand corner and Cartesian coordinates defined by the horizontal and vertical edges of the slide. Hence, the image data has a position within the coordinate system of an individual slide and each slide has a position within the coordinate system of the world view coordinate system.

Figure 8:
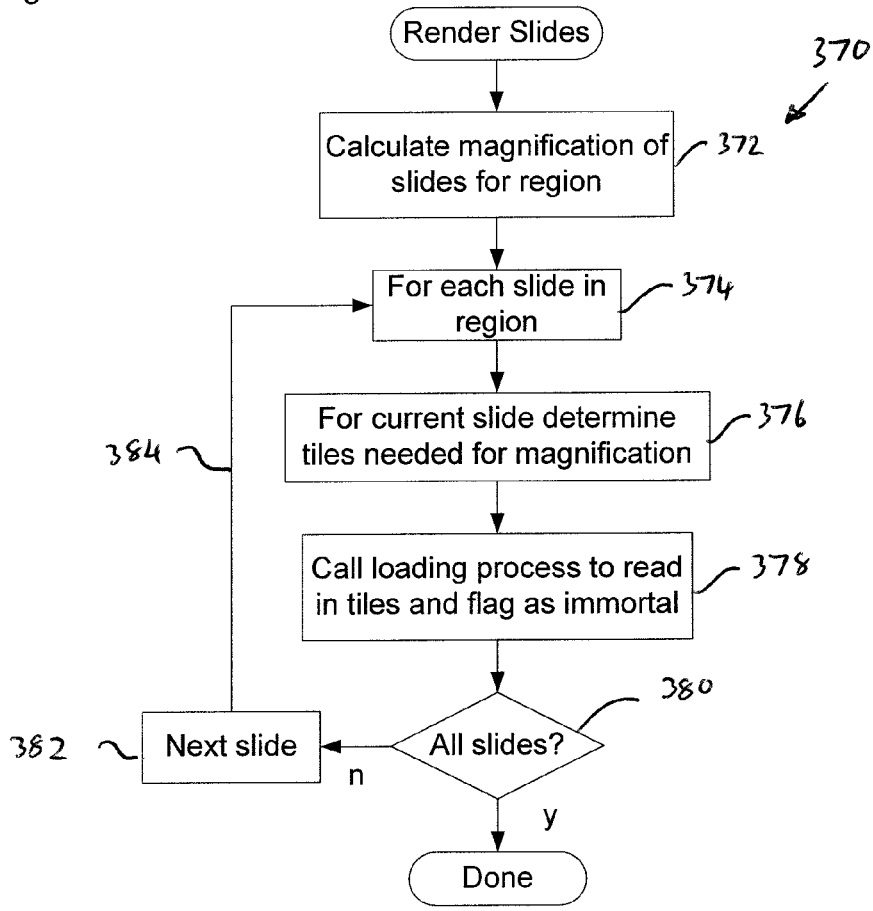
FIG. 8 shows a process flow chart illustrating a method of rendering slides in the viewer used in the method of FIG. 7.

FIG. 8 shows a process flow chart illustrating a slide rendering method 370 in greater detail. At step 372, the slide rendering method calculates a magnification for the slide images to be used to display the images such that all of the images will fit within the first display region 302. The viewer application 144 knows the size in pixels of the first region of the display device which extends from the bottom left hand corner 308 of region 302 to the far right hand side limit of the display region and to the upper limit of the display region. The viewer application also knows the size and position of each slide in the world co-ordinate system. From this, the viewer application calculates the bounds of the world that are occupied by any part of any slide and therefrom determines what level of magnification is required in order to fit all of the slides within the first slide display region 302.

Once the world view level of magnification has been determined at step 372, then processing proceeds to step 374 at which a data processing loop is started for all of the slides to be displayed in the first region. As mentioned above, slide image data is available at a number of different levels of magnification (as illustrated in FIG. 4), and the application selects the available level of magnification that is closest to the world view magnification. At step 376, the viewer application determines which tiles of the slide image for the selected magnification are required. As all of the slide is displayed in the first region, then all of the tiles for a particular level of magnification are selected at step 376. Then at step 378, the main programme thread of the viewer application calls a loading process, running in parallel to the main programme, instructing it to read in the required tiles. In parallel with the main programme flow, the loading process calls the server 136 with details of the tiles to be retrieved. Server 136 passes details of the particular slide and associated tiles to database server 138 which carries out a look-up in file store 140 and retrieves the image data for the particular tiles from file store 140. File store 140 returns the data for the identified tiles which are transmitted by viewer server 136 over network 134 to the loading process. The loading process then decompresses the received tiles of image data, if required, and loads them into local memory of client device 142 used by viewer application 144.

The viewer application has access to a data structure which is used as part of a memory management mechanism. The data structure lists details of each tile currently resident in memory. Associated with each tile loaded in memory is a status flag which flags whether that tile has the status of "immortal" or "dynamic" and also an indication of when the tile was last displayed. Those tiles flagged as "immortal" are persisted in memory and are not overwritten by new tiles. Those tiles flagged as "dynamic" are not persistently kept in memory and can be overwritten by new tile data when downloaded. Dynamic tile data is overwritten on an "oldest first" basis: i.e. the oldest unused (not displayed) tiles are overwritten by new tile data when required. By balancing the memory allocated to immortal tile data and dynamic tile data, it is possible to ensure that tile data is always available, at some level of magnification, for immediate display from local memory without memory becoming exhausted by the large amounts of image data.

During step 356, as all slides are to be rendered in the first world view image region 302, all of the tiles for all of the slides, at the appropriate level of magnification, are downloaded, stored in local memory, and flagged as immortal so that at least a low magnification image of any part of any of those slides will be available for display, if required. At step 380, it is determined whether all slides have been processed, and if not, then processing proceeds to step 382 at which the next slide is selected and process flow returns 384 to step 374 at which a next slide is selected for processing. Once all of the slides have been processed, then method 370 has completed.

Hence, the result of the completion of step 356 is the display of images 310, 312, 314, 316 at a low resolution in the world view region 302. Processing then proceeds to step 358 at which slides in the second, high magnification region 304 are rendered. Step 358 uses a slide rendering process similar to process 370 illustrated in FIG. 8 but with some modifications. At step 372, it is determined which of the available levels of magnification to use for displaying the higher resolution images in second region 304. The size of the second region 304 is determined by its width in pixels from an origin in the bottom left corner 320 and its maximal width at point 322 and its height by the size in pixel rows from the origin 320 and the upper limit of point 324. Hence, knowing the size, in display pixels, of the second display region 304, and the size and position in the world coordinate system of each slide to be displayed in that region, the viewer program determines which of the multiple levels of magnification will produce slide images most nearly fitting the display region 304. Then at step 374, a loop is begun for each slide at least partially displayed in display region 304. Then at step 376, for a currently selected slide, it is determined which of the tiles of that slide need to be displayed as falling within the second display region 304. For example, all of the tiles for slide 318 need to be displayed. However, for slide 320, the rightmost end part of the slide does not fall within the display region 304 and therefore tiles corresponding to that part of the slide do not need to be downloaded or displayed. Processing proceeds to step 378 at which the process is called to read in the tiles for the current slide, download those tiles, store in local memory, and flag as immortal. As explained above, tiles are flagged as immortal to prevent them being overwritten by newly downloaded tiles. However, those tiles can be deleted from memory when a new case is opened using the viewer. Therefore, at termination of the viewer, the memory management data structure is cleared so that no areas of memory are flagged as storing immortal tile data.

At step 380, it is determined whether all slides are least partially visible in the second region have been processed, and if not then at step 382 a next slide is selected and processing returns 384 to step 374 at which a next slide is selected for processing. Once all of the slides at least partially displayed in the second display region 304 have been processed, then step 358 is completed. The user interface of the viewer then has the appearance as illustrated in FIG. 5. As can be seen, low resolution images of all four slides are illustrated in the first world view region 302. High resolution images of the same four slides displayed in the second display region 304. At this stage, no images are displayed in the third display region 306.

At this stage, the user may view the virtual slide at the currently displayed magnifications, and the viewer is ready to receive user interaction.

While waiting for the user to interact, a further process is carried out by the main viewer programme in order to speed up the display of slides in the second region 304 at a magnification different to that at which they are currently displayed. This is referred to as a pre-fetching process in which image data likely to be used in displaying a different magnification level image of a slide or part of a slide is fetched and stored in local memory on the client device so as to reduce any lag in changes the view of the slides following user interaction. Hence, at step 360, image data for a different magnification level is fetched from the file store in case it is required for local rendering.

Figure 9:
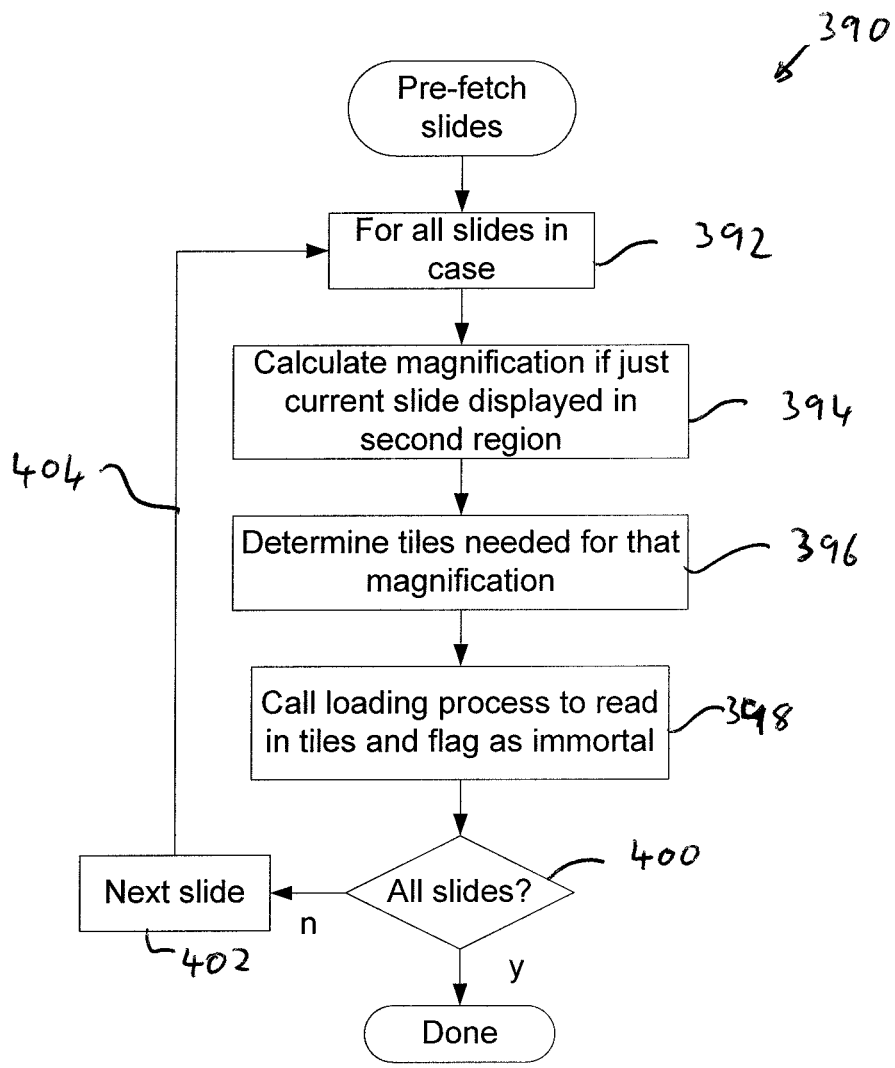
FIG. 9 shows a process flow chart illustrating a method of pre-fetching slides to be rendered in the viewer used in the method of FIG. 7.

FIG. 9 shows a process flow chart illustrating the image data pre-fetching method 390 in greater detail. At step 392, a processing loop is initiated over all of the slides in the case. At step 394, the method determines what magnification of a single slide to use if just the single slide were displayed in the second display region 304. Again, the size of the second display region in pixels and metadata about the size of each slide are used to determine which level of magnification most closely matches the slide to the second display region. Then at step 396, all of the tiles of the current slide for the selected magnification level are identified. Then at step 398, again the loading process is called to download the identified tiles from the file store, and read the image data for those tiles into memory. Those tiles are flagged as immortal, unless the case includes a large number of slides. In that case, tiles are flagged as dynamic once all of the memory allocated to immortal tile data is occupied. By flagging these tiles as immortal, a medium-resolution image of every slide is always available in local memory for the viewer to speed up rendering.

At step 400, it is determined whether the pre-fetching of tiles has been completed for all slides. If not, then at step 402 a next slide is selected and processing returns 404 to step 392 and a next slide is processed. The loop continues until all of the slides have been processed.

The opening of a case in the viewer has now completed.

The design of the viewer software allows the user to navigate seamlessly from the world view that shows the whole case to a high magnification view of an individual slide, or part of an individual slide, and any view in between. Navigation between different magnification views is possible with a negligible lag because the software has a low memory footprint (the memory overhead per tile is only a few hundred bytes) even though each slide typically requires hundreds of megabytes of disc space (more if uncompressed) and any one case may have more than 100 slides. Further, the provision of the world view allows the case as a whole to be assessed from the initial view illustrated in FIG. 5. Hence, using the world view 302, a user may more efficiently determine which of the plurality of slides to view first at high resolution.

For example, with reference to FIG. 5, from the initial view, it can be seen that slide 314 in world view 302 has some feature 315 within the tissue 317. Hence, the user may immediately determine that slide 314 is the first slide to be reviewed rather than having to sequentially work firstly through slides 310, 312 and then slide 314. Although a higher magnification version of slide 314 is displayed in second region 304 as slide 322, that high magnification view may not be sufficient for a user to carry out a suitable review of feature 315.

Figure 10:
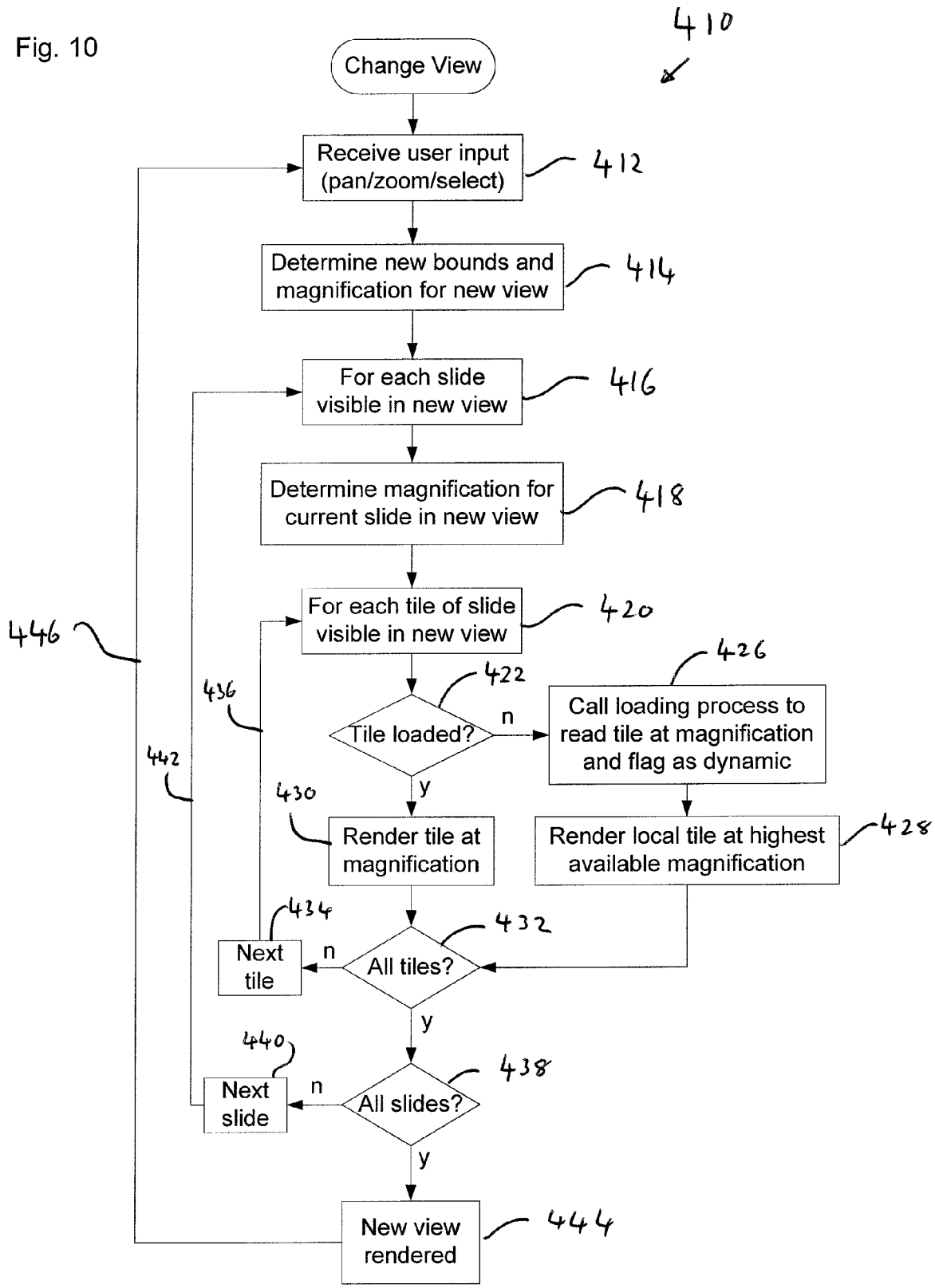
FIG. 10 shows a process flow chart illustrating a method changing the view of slides displayed in the viewer used in the method of FIG. 7.

A user may interact with the user interface in a number of ways in order to select a different view of the virtual slides. FIG. 10 shows a process flow chart illustrating a view changing method 410. A user may interact with the user interface by operating a control element to pan across, zoom in or out from, or select a region of the totality of slides as illustrated in the whole world view 302. Alternatively or additionally, a user may simply use a pointing device to select a region in the first view, or second view, by double clicking to zoom in at a point in the first region or second region, or to pan over the display tiles again in the first region or second region. Selecting to pan may involve a "drag" input as is familiar to those of skill in the user interface art.

Hence, at step 412, a user input is received indicating a pan, zoom or select command for a user. For example, the user might place a cursor closer to feature 315 in the second region 304 and double click.

At step 414, the corresponding bounds of the image of the slide at a higher level of magnification are determined From the user input, the viewer application calculates the position of the centre of region 304 in the world view coordinate system, and the width and height of the world that is shown in region 304 at the current zoom. The view centre, width and height are used to calculate the bounds of the world that are visible in the view. Then the view magnification is calculated from the width and height of the view in world coordinates, and the width and height of the display region in pixels.

At step 416, a loop is started over all of the slides wholly or partially visible within the new image boundary. Then, from a first one of those slides, at step 418, the level of magnification closest to the previously calculated magnification is determined. For that level of magnification, a loop is begun at step 420 for each of the tiles of the slide that will be visible in the second image region 304. At step 422, it is determined whether that tile is currently loaded into local memory. If not, then at step 426, the loading process is called to read the image data for that tile at the required level of magnification into local memory and flagged as dynamic. While the tile data is being downloaded, the viewer renders an image for that tile using the highest level of magnification currently available in local memory at step 428. Hence, in this way, some image is always presented to the user so that there are no blank parts of the image while data is being fetched. If the tile is locally available at step 422, then processing proceeds to step 430 which renders the tile data at the required magnification from the local memory. As the rendering process obtains the tile image data directly from local memory using a direct pointer to the memory location of the image data, then the access time is reduced thereby speeding up the rendering process.

At step 432, it is determined whether all tiles for the visible parts of the current slide have been rendered and if not then at step 434, a next tile is selected and processing returns 436 to step 420. Once all of the visible tiles have been rendered for the visible tiles of the current slide, then at step 438 it is determined whether all visible slides have been processed. If not, then at step 440, a next slide having at least a part visible in display region 304 is selected and processing returns 442 to step 416 at which the processing of the next slide is begun. When it is determined at step 438 that all slides having a part visible in second region 304 have been processed then at step 444, rendering of the new view has been completed and processing returns 446 to 412 where the viewer programme awaits further user input.

Figure 6:
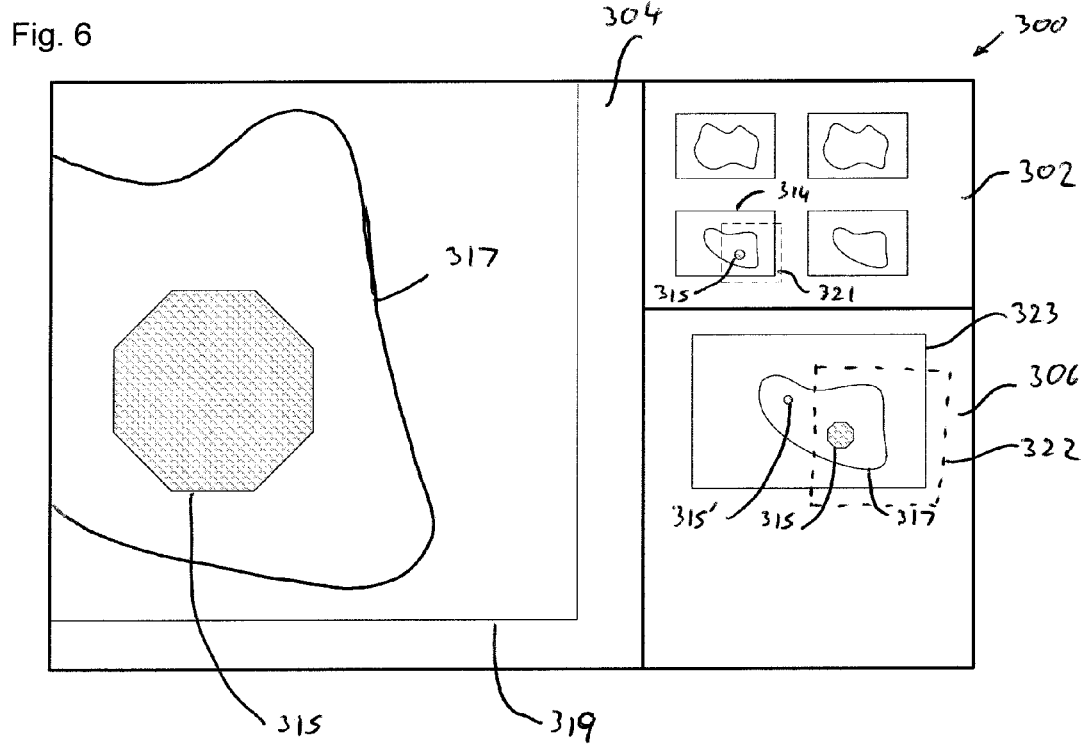
FIG. 6 shows a schematic visual representation of the user interface of the viewer illustrating a third image display region.

FIG. 6 illustrates the result of process 410. As can be seen, a higher magnification image 319 of a lower right hand portion of slide 314 has been displayed in second display region 304 of the user interface 300. Also a visible guide 321, in the form of a dashed line box, is overlaid on the portion of the first region 302 corresponding to the image displayed in the second region 304. Hence, visual guide 321 provides the user with extra information about the location in the world view of the part of the slide displayed in high magnification in the second region 304.

Further, a medium resolution image of the same slide has been rendered and displayed in the third region portion 306. The intermediate resolution image 323 is displayed using a process similar to that described in FIG. 10, but in which the relevant region is the size of the third region 306 rather than the second region 304. The intermediate resolution image 323 is at a magnification greater than that of images in the first region but lower than that of images in the second region 304. The intermediate magnification image 323 also provides some further navigational context to the user. Additionally, or alternatively, a further visible guide 322, also in the form of a dashed line box, is overlaid on the portion of the third region 306 corresponding to the image displayed in the second region 304. Hence, visual guide 322 provides the user with extra information about the location in intermediate magnification image 323 of the slide displayed in high magnification in the second region 304.

For example, a second feature 315' may also be present in tissue 317, but not easily discernable in image 314 nor displayed in image 319. However, it is easily viewable in image 323 and image 323 provides the user the mechanism for easily navigating to view a higher resolution image of feature 315' in second display region 304. For example, the user may double click on image 323 at a position adjacent to feature 315', or double click on image 314 or grab and drag image 317.

It will be appreciated that the planned navigation is carried out in a similar way but without any change in magnification. Instead, new bounds are simply determined for the new image and those tiles required to display the new area are determined but at the same magnification level as currently used in the second display region 304.

Hence, by using a pointing device and a cursor, the user can interact with any of the first, second or third image display regions to zoom in to different levels of magnification on any of the slides and view any of the different regions of any of the slides. There is always the world view display 302 providing a user with an overview of all slides in the case so that the user can more easily understand which part of which slide is currently being displayed in the higher magnification 304. Also, the intermediate magnification region 306 can provide useful intermediate level information assisting a user by displaying information not readily derivable from the images displayed in the first or second region. Hence, the user interface provides a far more efficient mechanism for allowing a user to quickly identify a priority for assessing different slides within a plurality of slides and always having visual information within which to orient themselves within the slides being displayed.

As discussed above, the world view of all slides of the case displayed in the display region 302 are automatically displayed upon opening the viewer. An aspect of the invention provides a method for determining the layout of slides so as to encode further information into that layout, and/or information presented within the individual slide images, to further facilitate use of the viewer for assessment purposes. While described in the context of the automatic layout of slides in the first region 302, the automatic layout of slides in a manner determined by assessment criteria or attributes may be applied more generally and is not limited only to the first display region of the user interface shown in FIG. 5.

Figure 11:
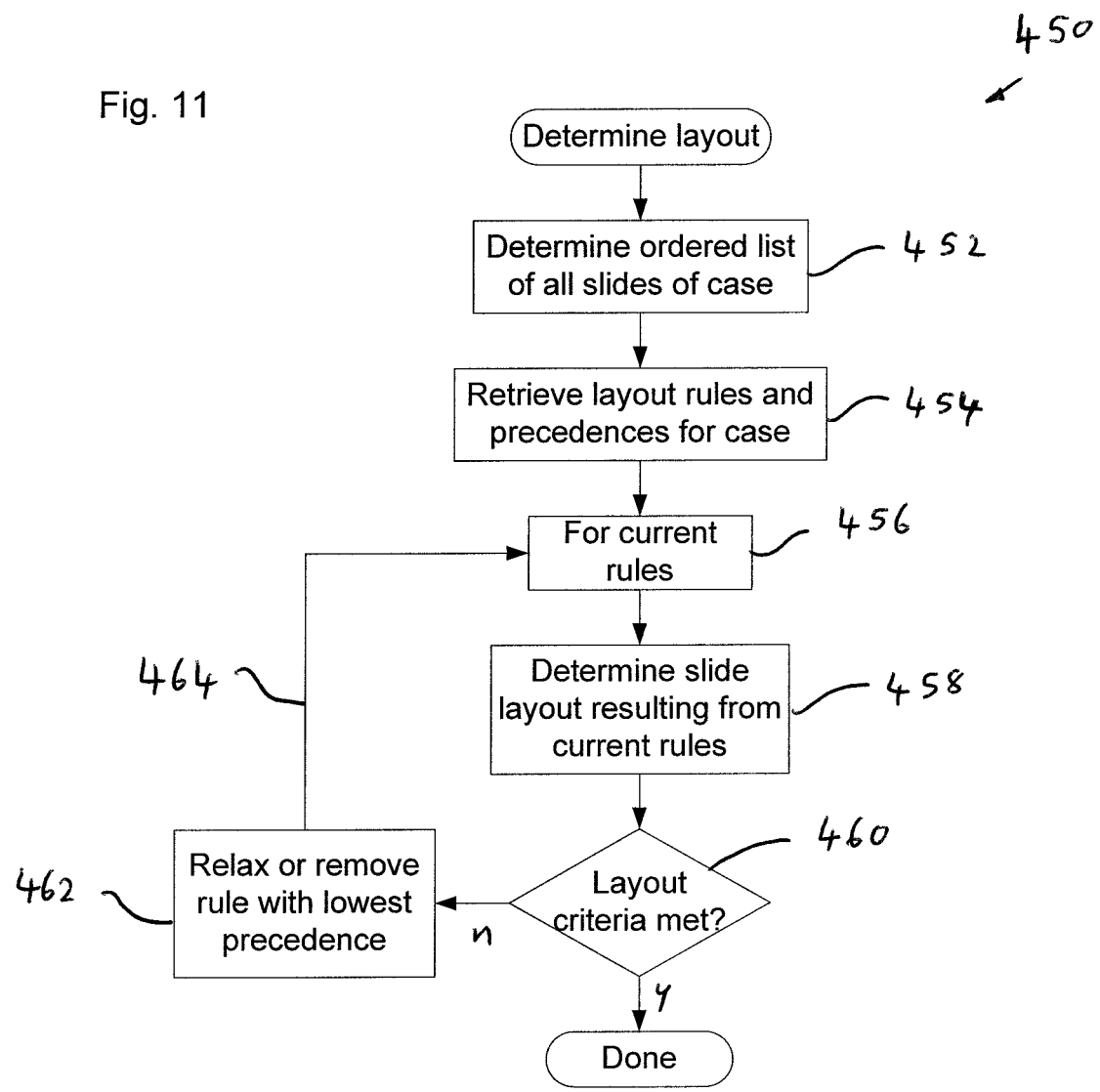
FIG. 11 shows a process flow chart illustrating a method of automatically determining a slide layout used when rendering slides in the viewer according to the invention.

FIG. 11 shows a process flow chart illustrating an automatic layout determining method 450 according to an aspect of the invention. FIG. 12 shows a visual representation of a slide layout 480 being a display region of the user interface 300. As discussed above, in some embodiments, slide layout 480 may correspond to the layout of slides in the first display region 302. FIG. 12 shows a result of process 450. As can be seen, the layout includes images of eight slides 482 to 496. Slides 482 to 492 are all tissue samples from the same part. Slides 494 and 496 show tissue samples from a second, different part.

Each virtual slide image includes a portion showing the stained tissue and also a header portion, e.g. header 498, having information relating to the tissue sample of the slide. Header portion 498 may include a first region 500 for displaying a description of the type of tissue displayed in the image. This information may be retrieved from the "Block Description" field of Block table 210 as described above. Header portion 498 may also include a second portion 502 for displaying information about the stain used to stain the tissue sample. Slides 482, 484 and 486 each have an image of a different tissue block from the same part. (In FIG. 12, "A1" designates block 1 of part A, "A2" block 2 of part A, and "B1", part 1 of block B, etc.) Slides 488, 490 and 492 each includes an image of the same tissue block, but wherein each tissue sample has been stained using a different stain. Hence, the description portion of header 504 is the same for each image but the stain information portion 506 is different for each tissue sample image.

Figure 12:
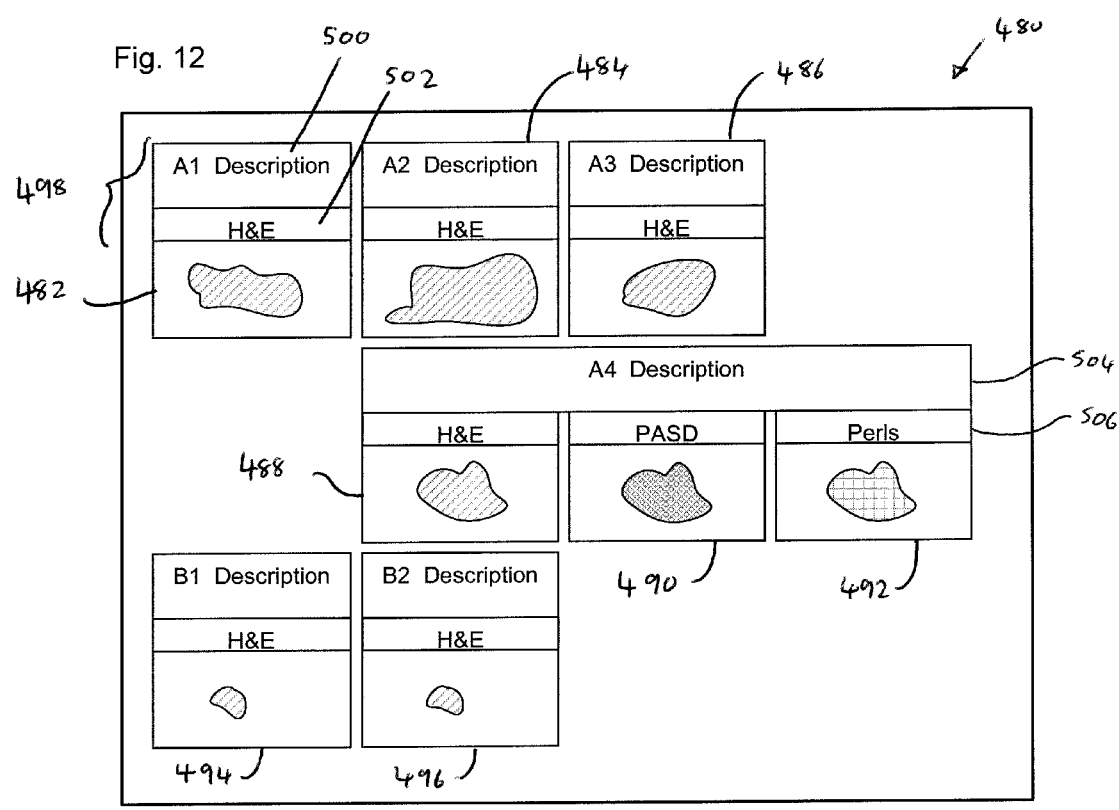
FIG. 12 shows a schematic visual representation of a part of the user interface of the viewer as displayed on a display device illustrating the method of FIG. 11.

The layout of the slide display of FIG. 12 is automatically determined by method 450 as follows. At step 452, the main viewer programme receives an ordered list of all the slides of the case. The slides of a case are ordered hierarchically according to the specimen, part, block, stain category, stain name and then slide number. The slide ordering rules can be user configurable, in absence of which, a default slide ordering is used. The data items required to order the slides are provided by the LIS when the viewer opens a case. The slide ordering itself can be performed by a simple algorithm similar to that used to sort columns of a spreadsheet according to multiple criteria. Once the hierarchically ordered list of slides has been determined at step 452, at step 454, the layout rules and precedence associated with the rules is retrieved for the current case. This can be user configurable data in the absence of which default settings can be used. An example set of case layout rules would comprise rules for the following. A rule may specify: which type of entity (specimen, part, block, stain category, stain name or slide number) signifies the beginning of a new paragraph in the layout. A rule may specify the indentation used for the first line of a paragraph (if any) and/or the indentation used for subsequent lines (if any). The indentation may be different for each entity type. The entity level at which slides should be grouped can also be specified by a rule. For example, all slides for a same block may be grouped together. For example, each group of slides may be placed on one line if possible, i.e. the number of group slides is less than or equal to the number that fits on one line. Grouping can be visually indicated by either containment (e.g. drawing a polygon around the slide), or connection (e.g. drawing one textual description for a plurality of slides) as illustrated in FIG. 12. A further rule may specify the scale (relative to glass size) at which the slide images should be displayed in the image display region and an associated tolerance. A further rule may specify the aspect ratio of the layout (height relative to width) and an associated tolerance. A precedence is associated with each rule used to define the case layout and indicates the least important to the most important rule. At step 456, a first version of the rules is determined and at step 458 the slide layout resulting from the current rule is determined.

At step 460, it is determined whether the current set out layout rules can be met within the size of the display region. If so, then the layout has been determined and the images of the slides can be rendered as described above. If the layout criteria cannot be met at step 460, then at step 462 the currently least important rule is either relaxed (e.g. its tolerance increased) or the lowest importance rule is removed from the rule set. Processing then returns 464 to step 456 and for the amended rule set, step 458 is repeated to determine a slide layout resulting from the amended rules. Processing continues to loop in this manner until a layout meeting the current rules is determined to be met at step 460. If none of the rules can be met, then a simple sequential matrix of thumbnail images at the lowest magnification is displayed in display region 480.

The virtual slide layout illustrated in FIG. 12 arises for a case with two parts (part A and part B) with samples from six blocks (A1, A2, A3, A4, B1 and B2) and eight slides. The slide layout rules comprise: a new paragraph for each different part, zero first line indentation, subsequent lines indented by one slide width and slides grouped by connection at the level of a block, in this case the three slides of block A4, slides 488, 490, 492. The aspect ratio of the display area is 4:3.

The layout rules allow clinically relevant information to be encoded into the slide layout to help a user more easily understand the relationship between slides owing to their relative position. Also, as the user can navigate amongst the higher magnification images by simply clicking on a one of the slide images, this provides an improved interface allowing the user to step directly between slides at any level in the hierarchy by a single interaction. The layout and interaction interact to reduce the time a user may take to locate and display the next slide which they need to review at a greater level of magnification. As the number of parts/blocks/levels/stains, etc in a particular case increases so does the time saving in allowing a user to directly navigate to the slide of most immediate interest.

As described above, a header portion of each slide image may be provided with clinical information relating to the sample displayed in the slide. That descriptive information helps to provide further relevant information to the user so that they can immediately determine exactly what the tissue sample relates to. For example, the clinical information may state explicitly exactly where the tissue was taken from. Further, the slide images can include information encoding the type of stain used to stain the tissue. This may be as simple as displaying text describing the stain (e.g. "H" and "E"). Alternatively or additionally, a portion or the whole of the slide may be colour coded to indicate the type of stain used. For example, stain information portion 506 may be displayed in a purple colour to designate slides with an H and E stain and slides using a special stain may be colour coded in green.

The layout rules may be user configurable such that a particular user may select the hierarchical way in which slides are to be laid out to meet with a particularly preferred workflow or a particularly preferred way to improve the efficiency with which they determine which slides to view first. Hence, the automated layout returning method 450 generates a display of a plurality of slides organised hierarchically by diagnostic criteria. The layout and other visual features of the slides are used to help maximise the information imparted visually to the user.

A further aspect of the invention will now be described which relates to combining images of tissue portions on separate slides. This may be applied to more than two images of tissue portions and the tissue portions may or may not come from the same original piece of material. In some instances, it may be useful to create a single virtual slide having image of tissue portions from different samples or specimens. For example, the samples or specimens may have come from different parts of the same patient, or the samples or specimens may have come from the same part of different patients. Hence, this aspect of the invention can be of benefit when it is desired to be able to handle a single virtual slide including at least two, or more, images of separate pieces of tissue, which may be from the same or from different original samples.

FIGS. 13 to 16 show visual representations of the various display regions of the user interface 510, 520, 530, 540 at different stages of the process. FIG. 17 shows a flowchart illustrating an image extract selection process 600 and FIG. 18 a flowchart illustrating an image extract manipulation process 630.

Before describing the process in detail, a brief overview will be given. In some cases, a single tissue sample may be too large for a single slide and may need to be cut into separate parts placed on separate slides. This is sometimes referred to as "making a composite block". However, it may be more convenient to assess the parts of the tissue when rejoined to constitute the whole of the tissue. The method of this aspect of the invention allows this to be carried out in a virtual way so as to provide a reconstituted single image of the original single piece of tissue. This is achieved by allowing a user to select those slides on which the different tissue part images are displayed. The user may then manipulate the images of the separate tissue parts by rotation and/or translation so as to reform the single tissue part. The reformed image of the single tissue part may then be manipulated as a single entity and viewed at different magnifications, selected and panned as per any other tissue image displayed by the viewer.

Figure 13:
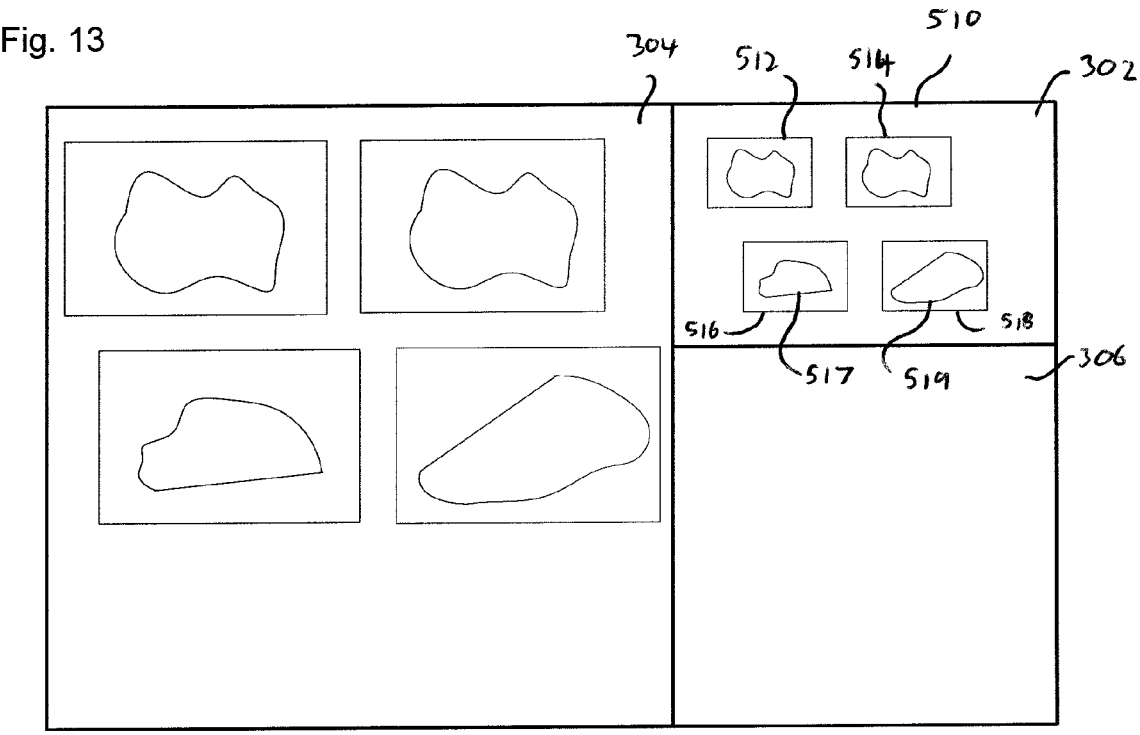
FIGS. 13 to 16 show a schematic visual representation of the user interface of the viewer as displayed on a display device at various stages of a 'glass melding' method of the invention.

This aspect of the invention is sometimes referred to herein as "glass melding" as it can be thought of as the virtual melding of two pieces of glass into a single piece of glass resulting in the two tissue samples being rejoined to reconstitute the original single tissue sample. FIG. 13 shows a schematic representation of the user interface 510 before beginning the glass melding process. Four virtual slides 512, 514, 516, 518 comprising all of the slides of the case, have been automatically laid out in the first display region 302 using the previously described process. A higher magnification view of the same four slides is provided in the second display region 304. Initially, nothing is displayed in the third display region 306. Slide 516 includes tissue sample part 517 and virtual slide 518 includes an image of second tissue part 519. Tissue parts 517 and 519 were originally the same single tissue sample which had to be cut, generally in half, in order to fit onto the original physical glass slides.

Figure 17:
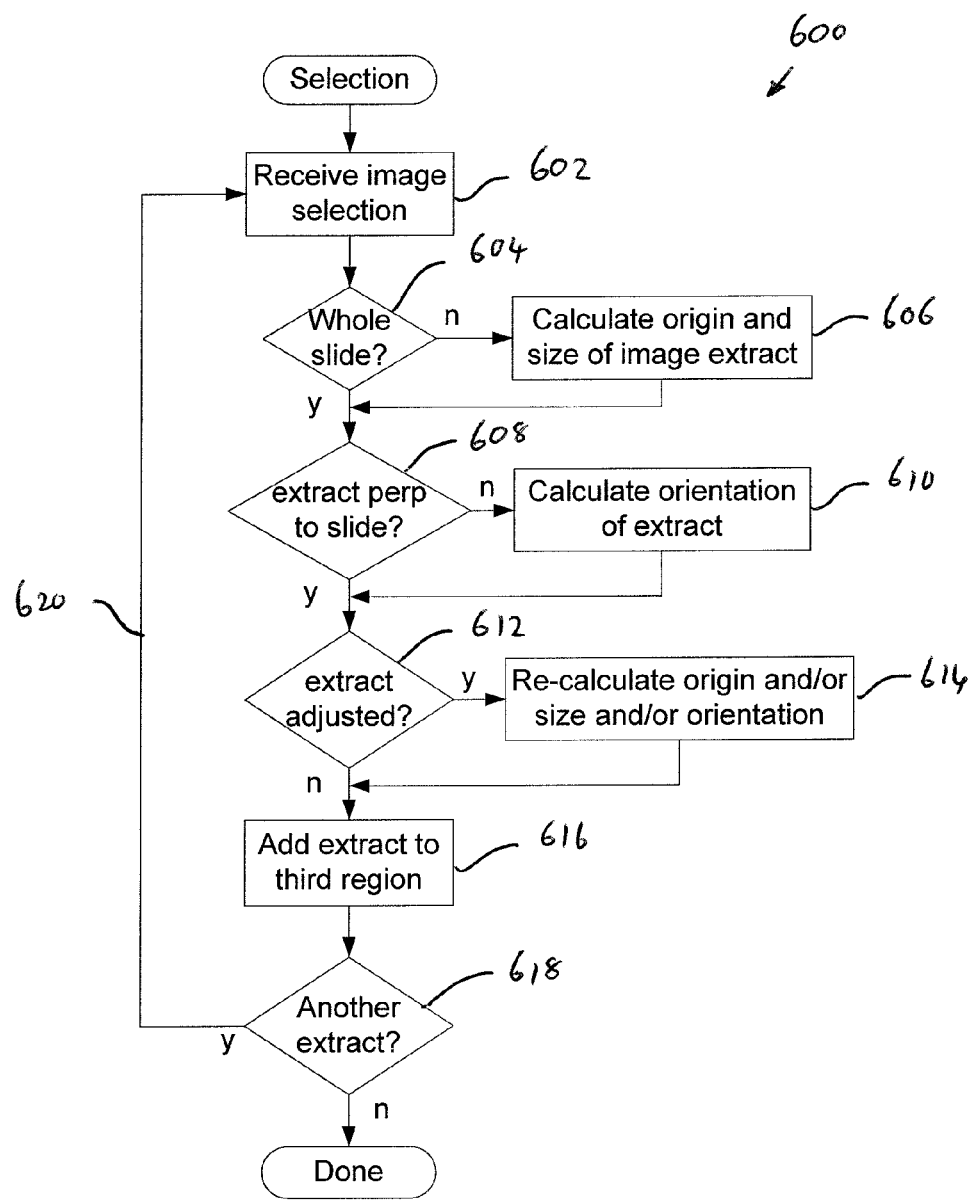
FIG. 17 shows a process flow chart illustrating an extract selection part of a 'glass melding' method according to the invention as illustrated in FIGS. 13 to 16.
Figure 18:
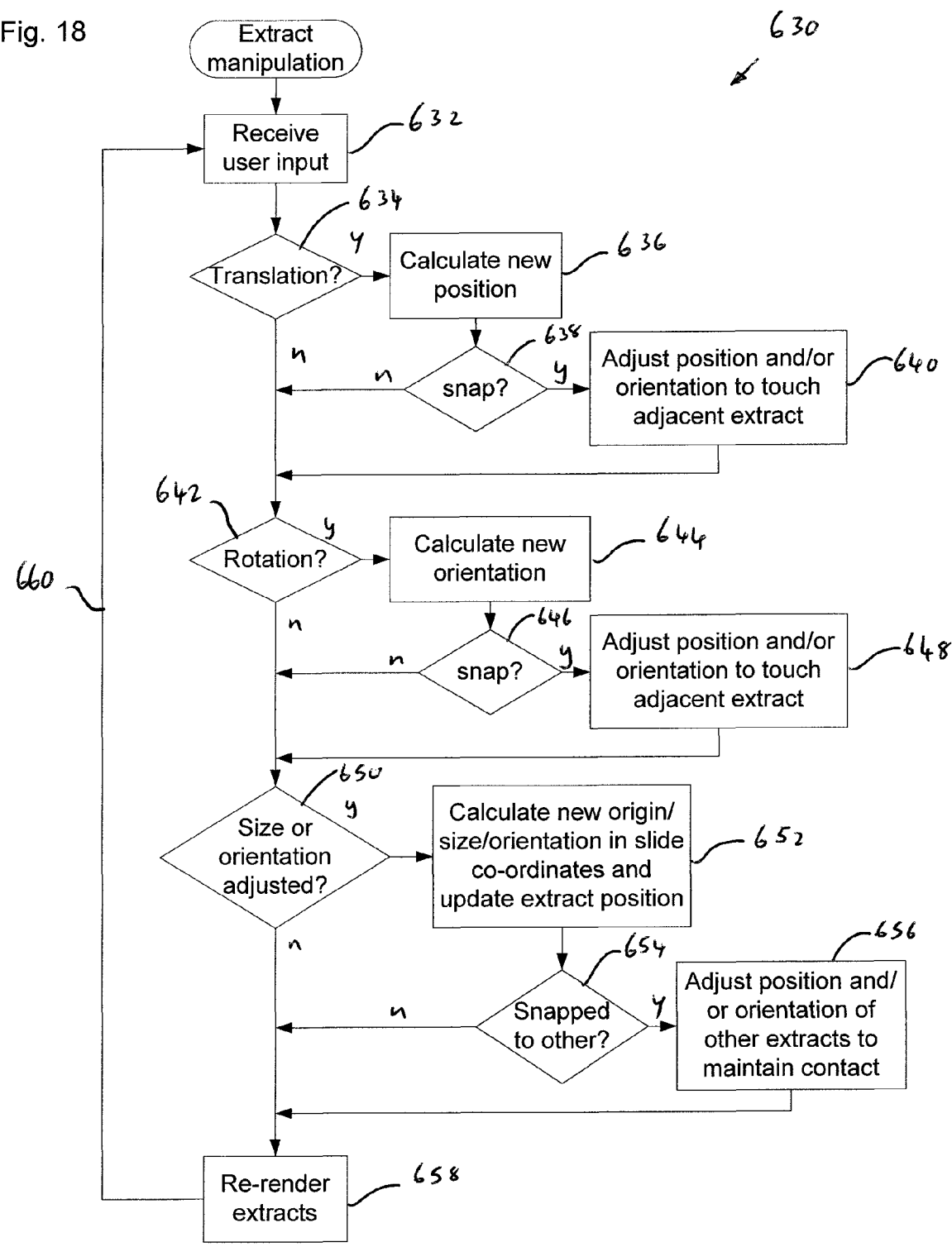
FIG. 18 shows a process flow chart illustrating an extract manipulation part of a 'glass melding' method according to the invention as illustrated in FIGS. 13 to 16.

The glass melding process includes the first general stage of selecting image extracts to be manipulated, followed by virtual manipulation of those sample image extracts in order to generate an image of the reconstituted single piece of tissue. FIG. 17 shows a process flowchart illustrating the image extract selection method 600. FIG. 18 shows a process flowchart illustrating the image extract manipulation method 630.

At step 602, the main programme thread of the viewer 144 receives user input to select a tissue image for subsequent manipulation. For example, this may include a user selecting a select image extract functionality and then clicking on the image of the tissue part 517 in display region 302. In other embodiments, this may include a grab and drag process in which the user selects the image of the tissue part 517 from the first display region 302 and drags that image into the third display region 306.

Irrespective of how the tissue extract image is selected at 602, method 600 proceeds to step 604 at which it is determined whether the user has selected the whole slide. If the user has not selected the whole slide, for example they have selected only the image of the tissue part or a part of the image of the tissue part 517, then at step 606, method 600 determines the origin within the slide coordinate system and size within the slide coordinate system of the image extract. As described above, each slide 512, 514, 516, 518 has its own internal slide coordinate system.

Then, at step 608, it is determined whether the image extract is perpendicular, or orthogonal to the major and minor axes of the slide, e.g. slide 516. An image processing algorithm can be used to determine the primary axes of the tissue extract image and hence the orientation of the extract relative to the slide's axes. If the primary axes of the tissue extract are not substantially parallel to the major and minor axes of the slide then at step 610 the orientation of the tissue extract relative to the slide axes is determined.

At step 612, it is determined whether the user has adjusted the image of the tissue extract. For example, a user may interactively drag elements, e.g. edges, of the tissue extract image to adjust the origin, size or orientation of the tissue image extract. For example, the user may increase the size of the tissue image extract in order to facilitate due to manipulation thereof. If the tissue from each extract is adjusted then at step 614, the origin and/or size and/or orientation of the tissue extract image are recalculated. Then at step 616, the tissue extract image is added to the third display region 306 and rendered therein.

Figure 14:
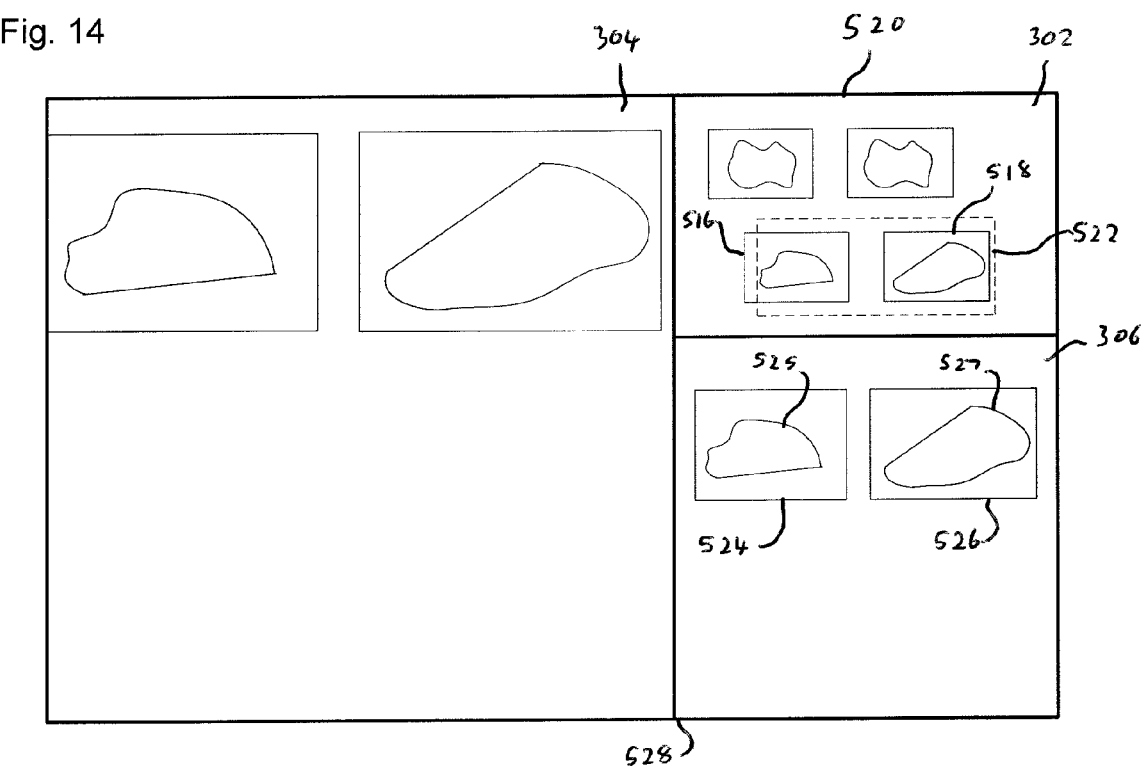

For example, in FIG. 14, a higher magnification image 524 of slide 516 is displayed in region 306 together with a higher magnification image 525 of tissue sample 517. The third display region 306 has its own Cartesian coordinate system with origin at point 528 and X and Y axes parallel to the lower and left hand side limits of the third display region 306. The data used by the viewer application to generate each extract image include the slide ID, the image extract origin, image extract size and image extract orientation in slide coordinates and the initial position and orientation in the third display region coordinate system. The third display region 306 may be referred to as a "sub-world" display region as it displays a part of the whole world displayed in the first display region 302.

At step 618, it is determined whether the user has selected another tissue image extract. If so, then processing returns 620 to 602 at which further user input is received. In this example, the user also selects the image of the second part of the original tissue sample 519 and drags that into the third display region 306. This results in display of a higher magnification image 526 of the original slide and a higher magnification image 527 of the tissue sample part 519.

As can also be seen in FIG. 14, a visual indicator 522 of the parts of slides 516 and 518 displayed in the second higher magnification display region 304 is also rendered in the first display region 302. Similarly, the second display region 304 is updated to show higher magnification images of only the selected parts of slides 516 and 518 therein.

Figure 15:
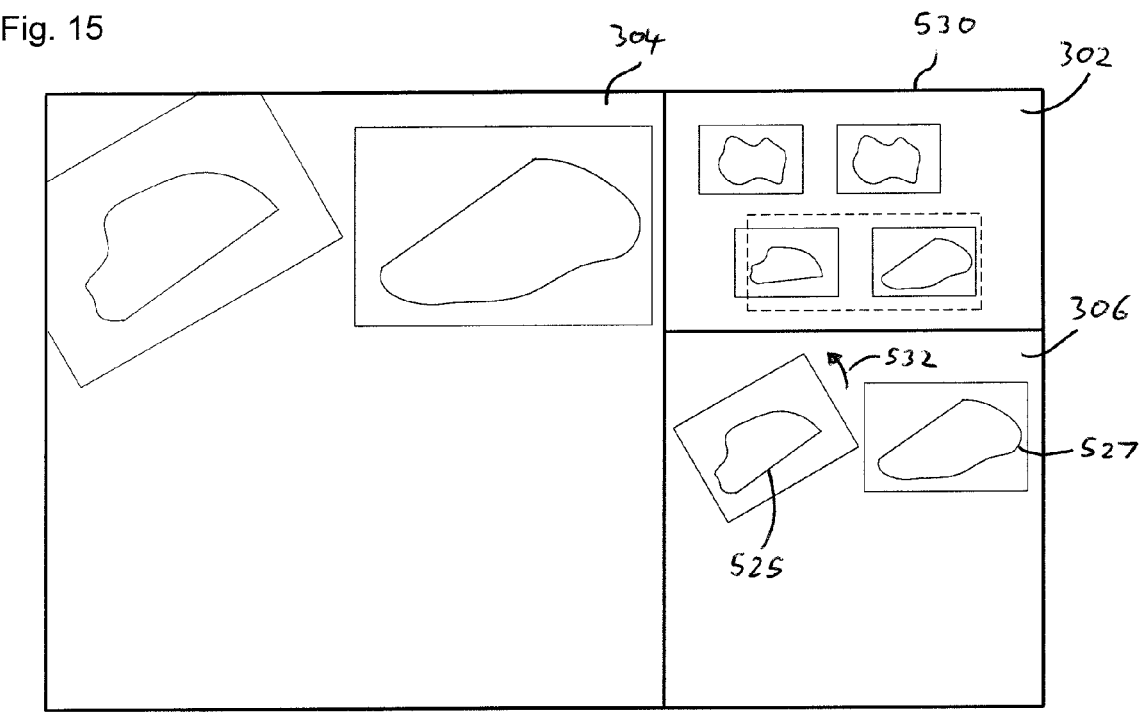
Figure 16:
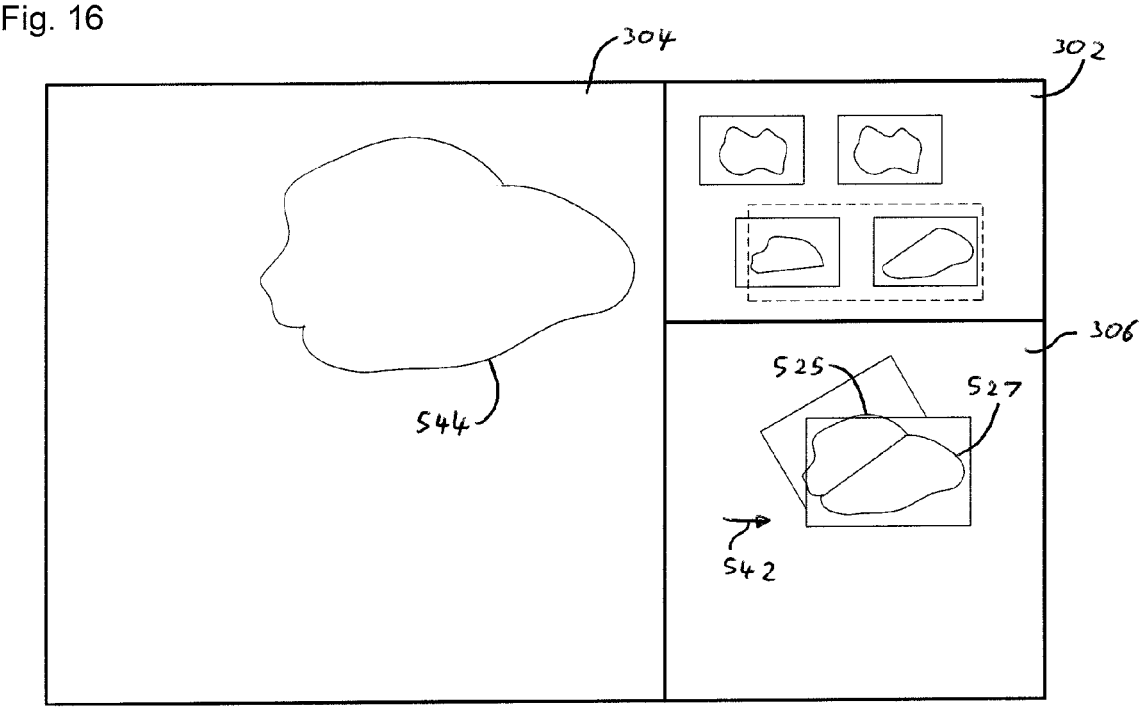

Referring to FIGS. 15, 16 and 18, manipulation of the tissue image extracts may now be carried out. At 632, user input is received. At 634 it is determined whether the user input corresponds to a translation of the tissue image extract. A user may manipulate the tissue image extracts in third region 306 by using a cursor to drag the images to cause translation in the XY plane. A handle may be provided to allow rotation of the images when that handle is grabbed by the cursor. Alternatively, ancillary control elements may be provided in the user interface to allow rotation or translation of the tissue image extract. If user input corresponding to the translation is determined to have been received at 634, then at 636 a new position in the coordinate system of the third display region 306 is calculated. An automatic "snap to" functionality can be provided in which a tissue image extract snaps to any adjacent tissue image extract. If it is determined that there is no sufficiently close tissue image extract to snap to then processing proceeds to step 642 otherwise at 638, a snap function is carried out and the position and/or orientation of the currently manipulated tissue image extract are adjusted so as to touch an adjacent image extract at 640. The position and/or orientation of the tissue image extract in the third display region coordinate system are updated.

Processing then proceeds to step 642 at which it is determined whether a rotation user input has been received. If not, then processing proceeds to step 650. If a rotation command user input has been received, then processing proceeds to step 644 at which the orientation of the currently manipulated tissue image extract is newly calculated. Again, it is determined at 646 whether to snap the currently manipulated tissue image extract to an adjacent image extract. If a snap is not determined to be needed at 646 then processing proceeds to step 650 otherwise, at 648, the position and/or orientation of the currently manipulated image extract are adjusted so as to touch the adjacent tissue image extract. Again, the position and orientation of the currently manipulated tissue image extract in the third display region coordinate system are updated.

For example, FIG. 15 illustrates a rotation of the first tissue image extract 525, as illustrated by arrow 532. FIG. 16 illustrates a translation of the first tissue image extract, as illustrated by arrow 542 so that the first tissue image extract 525 and second tissue image extract 527 are brought together to reconstitute the original single piece of tissue.

When the image of the single piece of tissue has been reconstituted, then its size or orientation can be manipulated in order to facilitate assessment of the tissue sample image. At step 650, it is determined whether user input is received to adjust the size or orientation of the image of the single tissue piece. If not, then processing proceeds to step 658 at which the images of the tissue pieces are re-rendered based on the manipulation carried out.

If at 650 it is determined that the size or orientation of the image of the single piece of tissue have been adjusted, then a new origin, size or orientation of the selected tissue image extract are calculated in the slide coordinate system for that tissue image extract. Also, the position of the tissue image extract in the third display region coordinate system is also updated. At step 654 it is determined whether the manipulated tissue image extract is snapped to another. If not, then processing proceeds to step 658. If, as illustrated in FIG. 16, the currently manipulated tissue image extract is snapped to another image extract, in this example 527, then the position and/or orientation of the snapped to tissue image extract are also updated to maintain contact with the manipulated tissue image extract. Processing then returns to step 658 at which the images of the tissue image extracts are re-rendered appropriately.

Hence, for example, at 650, it is possible for a user to select to increase the size of, or change the orientation or position, of a one of the image extracts and for a second image extract snapped thereto to also be increased and repositioned so that the user may manipulate effectively a single image of the original piece of tissue. Hence, as illustrated in FIG. 16, in the main display region 304, a single image 544 of the tissue sample is displayed at a higher magnification.

As described previously, the user may then manipulate that image by zooming, panning or otherwise manipulating the image so as to review the image at any level of magnification and any position within the tissue image. This therefore allows a user to manipulate a single image of the reconstituted single piece of tissue rather than having to manipulate separate images in order to assess the single piece of tissue.

In order to render the image extracts in the third display region 306, the position and orientation of the extracts in the third display region coordinate system are transformed and the part of the extracts image that is defined by the extract origin, extract size and extract orientation in the slide coordinates system are used to render the tissue image in the third display region 306.

The melding glass functionality allows arbitrary extracts from any of the slides of a case to be interactively assembled in a further display region. The further display region is defined parametrically in terms of the original slides in real time. This means that a copy of the slides does not have to be created. The slides may be viewed, panned, zoomed, etc in real time and the parameters of the resulting single image may be stored for future use. This allows the user to review key tissue samples of a case together rather than scattered amongst different slides. This can improve diagnosis and teaching. By storing details of the fused images, the extracts may be displayed and referred to at a later date, e.g. for a second opinion or during teaching. Hence, the ability to meld virtual slides using the viewer greatly facilitates interpretation of the two images.

Generally, embodiments of the present invention, and in particular the processes involved in displaying the images in the viewer, employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) in non-transitory form for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 19:
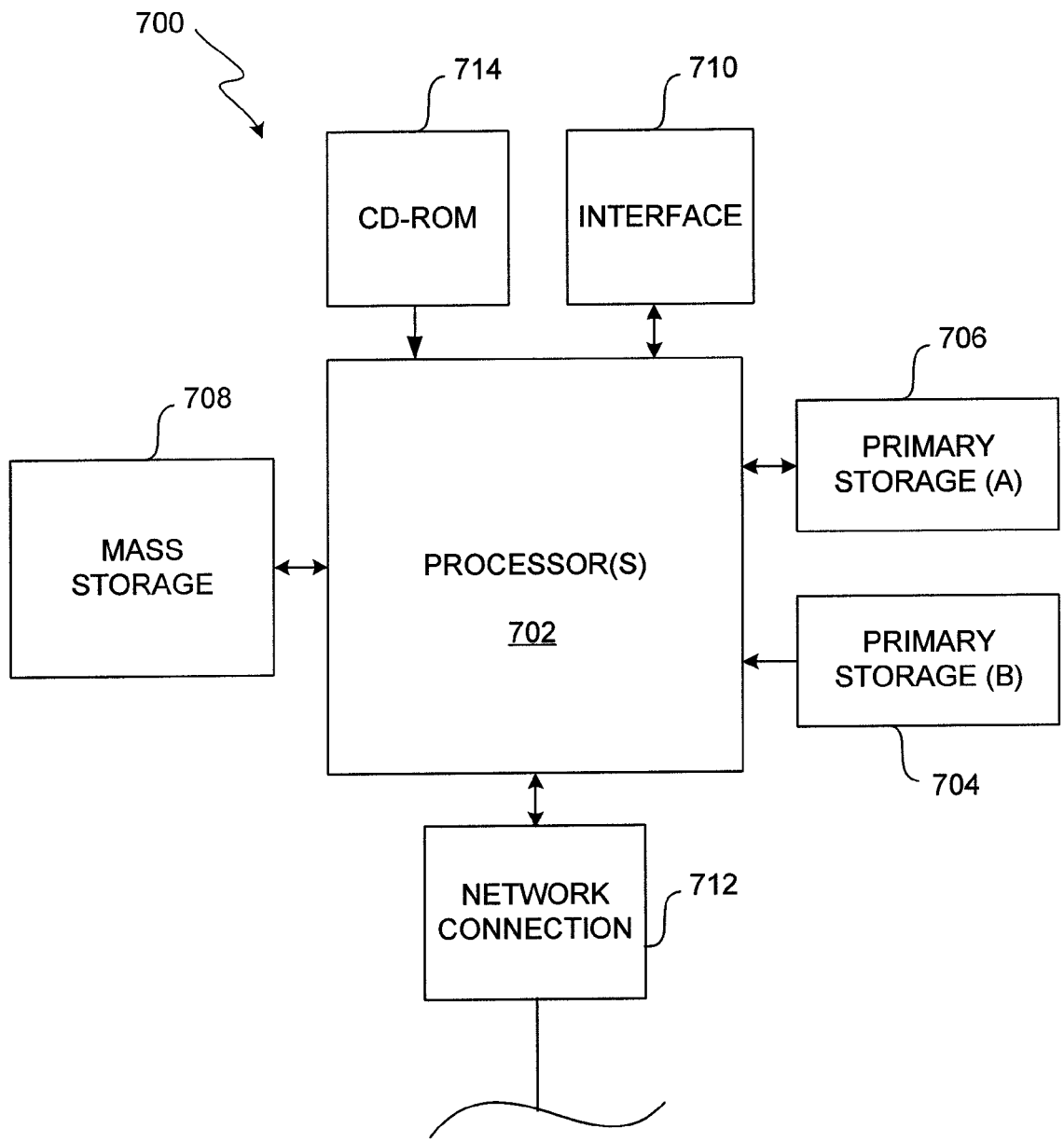
FIG. 19 shows a schematic block diagram of a viewer data processing device according to the system and being part of the computer system shown in FIG. 2.

FIG. 19 illustrates a typical computer device or data processing device that, when appropriately configured or designed, can serve as a viewer apparatus of this invention. The data processing device 700 includes any number of processors 702 (also referred to as central processing units, or CPUs) that are coupled to storage devices including primary storage 706 (typically a random access memory, or RAM), primary storage 704 (typically a read only memory, or ROM). CPU 702 may be of various types including microcontrollers and microprocessors such as programmable devices (e.g., CPLDs and FPGAs) and unprogrammable devices such as gate array ASICs or general purpose microprocessors. As is well known in the art, primary storage 704 acts to transfer data and instructions uni-directionally to the CPU and primary storage 706 is used typically to transfer data and instructions in a bi-directional manner. Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk. It will be appreciated that the information retained within the mass storage device 708, may, in appropriate cases, be incorporated in standard fashion as part of primary storage 706 as virtual memory. A specific mass storage device such as a CD-ROM 714 may also pass data uni-directionally to the CPU.

CPU 702 is also coupled to an interface 710 that connects to one or more input/output devices such as such as display devices, video monitors, track balls, mice, keyboards, microphones, pointer devices, touch-sensitive displays, transducer card readers, magnetic or paper tape readers, tablets, styluses, voice or handwriting recognizers, or other well-known input devices such as, of course, other computers. Finally, CPU 702 optionally may be coupled to an external device such as a database or a computer or telecommunications network using an external connection as shown generally at 712. With such a connection, it is contemplated that the CPU might receive information from the network, or might output information to the network in the course of performing the method steps described herein.

Although the above has generally described the present invention according to specific processes and apparatus, the present invention has a much broader range of applicability. In particular, aspects of the present invention is not limited to any particular kind of material or image and can be applied to virtually any type of digital image where multiple associated images are to be displayed to assist in assessing the information provided by those images. Thus, the invention is not limited only to virtual microscopy or pathology applications, and in some embodiments, the techniques of the present invention could provide information about many different types of materials using digital images of those materials generated in ways other than scanning. One of ordinary skill in the art would recognize other variants, modifications and alternatives in light of the foregoing discussion.

What is claimed is:

1. A method for displaying virtual slide images on a display device of a virtual slide viewing device, comprising:
   automatically displaying images of a first plurality of separate physical slides in a first region of the display device having a first area and at a first magnification, wherein said first plurality of slides are associated;
   displaying an image of at least a part of each of a second plurality of slides of the first plurality of slides in a second region of the display device at a second magnification, wherein said second magnification is greater than said first magnification;
   receiving user input to the virtual slide viewing device; and
   panning the image displayed in the second region responsive to said user input to correspond to a different position of the first area and wherein the different position is anywhere within the first area.

2. The method of claim 1, wherein the plurality of slides include material from one specimen or a plurality of specimens.

3. The method of claim 1, further comprising:
   displaying an image of at least a part of at least one of the first plurality of slides in a third region of the display device at a third magnification, wherein said third magnification is greater than said first magnification and less then said second magnification.

4. The method of claim 3, wherein the first plurality of slides in the first region have a layout pattern, an image of at least a part of a plurality of the first plurality of slides is displayed in the third region of the display device at the third magnification and wherein the image of at least a part of each of the plurality of the first plurality of slides in the third region has the same layout pattern.

5. The method of claim 3, wherein said user input is generated by a cursor being positioned in, or user interaction with, the first region or the second region or the third region.

6. The method of claim 1, wherein said user input is selected from: a zoom command; and a select command.

7. The method of claim 1, wherein said user input is generated by a cursor being positioned in, or user interaction with, the first region or the second region.

8. The method of claim 1, further comprising:
displaying a visual indication in the first region of those parts of the first plurality of slides displayed in the first region which are also currently being displayed in the second region.

9. The method of claim 1, further comprising:
loading a plurality of different portions of image data into local memory of the virtual slide viewing device; and
flagging at least one of the portions of image data as persistent so that the portion of image data is not overwritten while the current first plurality of slides are being displayed.

10. The method of claim 9, further comprising:
flagging at least one of the portions of image data as non-persistent so that the portion of image data can be overwritten while the current first plurality of slides are being displayed.

11. The method of claim 1, wherein image data for each virtual slide is stored at a plurality of different levels of magnification.

12. The method of claim 11, wherein the image data for each different level of magnification is divided into a plurality of different portions of image data.

13. The method of claim 12, wherein displaying an image of at least a part of each of the second plurality of slides in a second region of the display device comprises reading only those portions of image data corresponding to parts of each of the second plurality of slides visible in the second region.

14. The method of claim 12, further comprising storing a pointer to a location in local memory at which the portion of image data is stored, for each of a plurality of portions of image data.

15. The method of claim 1, further comprising:
persistently storing in local memory all the image data required to display all of the first plurality of slides in the second region at a particular level of magnification while the viewer is being used to display the first plurality of slides.

16. The method of claim 1, further comprising:
loading into local memory of the image viewing device image data for the first plurality of slides at a level of magnification different to the level of magnification currently being used in the second region while said image of at least a part of each of the second plurality of slides is being displayed in the second region.

17. The method of claim 1, further comprising:
downloading image data for the first plurality of slides from a remote storage device over a network.

18. The method of claim 1, wherein after receiving user input to the virtual slide viewing device, the method further comprises changing the magnification of the image displayed in the second region responsive to said user input to a third magnification, wherein said third magnification is greater than said first magnification and different to said second magnification.

19. The method of claim 1 wherein each slide of the first plurality of slides is spaced apart from any other slide.

20. A virtual slide image viewing device, comprising:
a display device; and
a data processing device in communication with the display device, wherein the data processing device is configured to carry out the method of claim 1.

21. A non-transitory computer readable medium storing computer program code which when loaded into a data processing device configures the data processing device to carry out the method of claim 1.

22. A method for displaying virtual slide images on a display device of a virtual slide viewing device, comprising:
automatically displaying images of a first plurality of separate physical slides in a first region of the display device having a first area and at a first magnification, wherein said first plurality of slides are associated;
displaying an image of at least a part of each of a second plurality of slides of the first plurality of slides in a second region of the display device at a second magnification, wherein said second magnification is greater than said first magnification and wherein the first plurality of slides in the first region have a layout pattern and wherein the image of at least a part of each of the second plurality of slides in the second region has the same layout pattern;
receiving user input to the virtual slide viewing device; and
panning the image displayed in the second region responsive to said user input to correspond to a different position of the first area and wherein the different position is anywhere within the first area.

* * * * *